United States Patent
Schurman et al.

(10) Patent No.: US 9,554,737 B2
(45) Date of Patent: *Jan. 31, 2017

(54) NONINVASIVELY MEASURING ANALYTE LEVELS IN A SUBJECT

(71) Applicant: GLT Acquisition Corporation, Irvine, CA (US)

(72) Inventors: Matthew J. Schurman, Richboro, PA (US); Walter J. Shakespeare, Macungie, PA (US); William Henry Bennett, San Jose, CA (US)

(73) Assignee: MASIMO CORPORATION, Irvine, CA (US)

( * ) Notice: Subject to any disclaimer, the term of this patent is extended or adjusted under 35 U.S.C. 154(b) by 382 days.

This patent is subject to a terminal disclaimer.

(21) Appl. No.: 14/036,786

(22) Filed: Sep. 25, 2013

(65) Prior Publication Data

US 2014/0094667 A1  Apr. 3, 2014

Related U.S. Application Data

(63) Continuation of application No. 13/229,410, filed on Sep. 9, 2011, now Pat. No. 8,548,549, which is a (Continued)

(51) Int. Cl.
 *A61B 5/1455* (2006.01)
 *A61B 5/00* (2006.01)
 *A61B 5/145* (2006.01)

(52) U.S. Cl.
 CPC ........... *A61B 5/1455* (2013.01); *A61B 5/0066* (2013.01); *A61B 5/14532* (2013.01); *A61B 2560/0223* (2013.01)

(58) Field of Classification Search
 CPC .............. A61B 5/1455; A61B 5/14551; A61B 5/14532

(Continued)

(56) References Cited

U.S. PATENT DOCUMENTS

| 3,826,905 A | 7/1974 | Valkama et al. |
| 3,958,560 A | 5/1976 | March |

(Continued)

FOREIGN PATENT DOCUMENTS

| EP | 0282234 | 9/1988 |
| EP | 0160768 | 5/1989 |

(Continued)

OTHER PUBLICATIONS

Arnold. M.A. et al., "Determination of Physiological Levels of Glucose in an Aqueous Matrix with Digitally Filtered Fourier Transform Near-Infrared Spectra," Anal. Chem. 64(14):1457-64 (1990).

(Continued)

*Primary Examiner* — Tse Chen
*Assistant Examiner* — Chu Chuan (JJ) Liu
(74) *Attorney, Agent, or Firm* — Knobbe, Martens, Olson & Bear LLP

(57) ABSTRACT

A method for noninvasively measuring analyte levels includes using a non-imaging OCT-based system to scan a two-dimensional area of biological tissue and gather data continuously during the scanning. Structures within the tissue where measured-analyte-induced changes to the OCT data dominate over changes induced by other analytes are identified by focusing on highly localized regions of the data curve produced from the OCT scan which correspond to discontinuities in the OCT data curve. The data from these localized regions then can be related to measured analyte levels.

21 Claims, 10 Drawing Sheets

Related U.S. Application Data continuation of application No. 11/445,631, filed on Jun. 2, 2006, now Pat. No. 8,036,727, which is a continuation-in-part of application No. 10/916,236, filed on Aug. 11, 2004, now Pat. No. 7,254,429.

(60) Provisional application No. 60/686,721, filed on Jun. 2, 2005.

(58) Field of Classification Search
USPC ....... 600/310, 316, 322, 323, 326, 340, 473, 600/476
See application file for complete search history.

(56) References Cited

U.S. PATENT DOCUMENTS

| | | |
|---|---|---|
| 4,014,321 A | 3/1977 | March |
| 4,476,875 A | 10/1984 | Nilsson et al. |
| 4,590,948 A | 5/1986 | Nilsson |
| 4,606,351 A | 8/1986 | Lubbers |
| 4,655,225 A | 4/1987 | Dahne et al. |
| 4,704,029 A | 11/1987 | Van Heuvelen |
| 4,731,363 A | 3/1988 | Hamilton et al. |
| 4,743,604 A | 5/1988 | Alig et al. |
| 4,746,211 A | 5/1988 | Ruth et al. |
| 4,750,830 A | 6/1988 | Lee |
| 4,834,111 A | 5/1989 | Khanna et al. |
| 4,871,755 A | 10/1989 | Alig et al. |
| 4,873,989 A | 10/1989 | Einzig |
| 4,882,492 A | 11/1989 | Schlager |
| 4,883,953 A | 11/1989 | Koashi et al. |
| 4,890,621 A | 1/1990 | Hakky et al. |
| 4,901,728 A | 2/1990 | Hutchinson |
| 4,948,248 A | 8/1990 | Lehman |
| 4,960,128 A | 10/1990 | Gordon et al. |
| 4,964,408 A | 10/1990 | Hink et al. |
| 4,979,509 A | 12/1990 | Hakky |
| 4,989,978 A | 2/1991 | Groner |
| 5,025,785 A | 6/1991 | Weiss |
| 5,028,787 A | 7/1991 | Rosenthal et al. |
| 5,041,187 A | 8/1991 | Hink et al. |
| 5,054,487 A | 10/1991 | Clarke |
| 5,069,213 A | 12/1991 | Polczynski |
| 5,070,874 A | 12/1991 | Barnes et al. |
| 5,101,814 A | 4/1992 | Palti |
| 5,112,124 A | 5/1992 | Harjunmaa et al. |
| 5,115,133 A | 5/1992 | Knudson |
| 5,163,438 A | 11/1992 | Gordon et al. |
| 5,168,325 A | 12/1992 | Yoder-Short |
| 5,178,153 A | 1/1993 | Einzig |
| 5,209,231 A | 5/1993 | Cote et al. |
| 5,222,495 A | 6/1993 | Clarke et al. |
| 5,222,496 A | 6/1993 | Clarke et al. |
| 5,243,983 A | 9/1993 | Tarr et al. |
| 5,267,152 A | 11/1993 | Yang et al. |
| 5,277,181 A | 1/1994 | Mendelson et al. |
| 5,278,627 A | 1/1994 | Aoyagi et al. |
| 5,313,941 A | 5/1994 | Braig et al. |
| 5,319,355 A | 6/1994 | Russek |
| 5,321,501 A | 6/1994 | Swanson et al. |
| 5,337,744 A | 8/1994 | Branigan |
| 5,341,805 A | 8/1994 | Stavridi et al. |
| 5,348,003 A | 9/1994 | Caro |
| 5,349,953 A | 9/1994 | McCarthy et al. |
| 5,361,758 A | 11/1994 | Hall et al. |
| D353,195 S | 12/1994 | Savage et al. |
| D353,196 S | 12/1994 | Savage et al. |
| 5,370,114 A | 12/1994 | Wong et al. |
| 5,372,136 A | 12/1994 | Steuer et al. |
| 5,376,336 A | 12/1994 | Lubbers et al. |
| 5,377,676 A | 1/1995 | Vari et al. |
| 5,379,238 A | 1/1995 | Stark |
| 5,383,452 A | 1/1995 | Buchert |
| 5,398,681 A | 3/1995 | Kupershmidt |
| D359,546 S | 6/1995 | Savage et al. |
| 5,431,170 A | 7/1995 | Mathews |
| 5,433,197 A | 7/1995 | Stark |
| 5,435,309 A | 7/1995 | Thomas et al. |
| D361,840 S | 8/1995 | Savage et al. |
| D362,063 S | 9/1995 | Savage et al. |
| 5,448,992 A | 9/1995 | Kupershmidt |
| 5,452,716 A | 9/1995 | Clift |
| 5,452,717 A | 9/1995 | Branigan et al. |
| D363,120 S | 10/1995 | Savage et al. |
| 5,456,252 A | 10/1995 | Vari et al. |
| 5,457,535 A | 10/1995 | Schmidtke et al. |
| 5,459,570 A | 10/1995 | Swanson et al. |
| 5,479,934 A | 1/1996 | Imran |
| 5,482,036 A | 1/1996 | Diab et al. |
| 5,490,505 A | 2/1996 | Diab et al. |
| 5,492,118 A | 2/1996 | Gratton et al. |
| 5,494,043 A | 2/1996 | O'Sullivan et al. |
| 5,501,226 A | 3/1996 | Petersen et al. |
| 5,533,511 A | 7/1996 | Kaspari et al. |
| 5,534,851 A | 7/1996 | Russek |
| 5,535,743 A | 7/1996 | Backhaus et al. |
| 5,549,114 A | 8/1996 | Petersen et al. |
| 5,551,422 A | 9/1996 | Simonsen et al. |
| 5,553,616 A | 9/1996 | Ham et al. |
| 5,561,275 A | 10/1996 | Savage et al. |
| 5,562,002 A | 10/1996 | Lalin |
| 5,582,168 A | 12/1996 | Samuels et al. |
| 5,582,171 A | 12/1996 | Chornenky et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,710,630 A | 1/1998 | Essenpreis et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,795,295 A | 8/1998 | Hellmuth et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,036,919 A | 3/2000 | Thym et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,147,108 A | 11/2000 | Hauptman |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,173,197 B1 | 1/2001 | Boggett et al. |
| 6,184,521 B1 | 2/2001 | Coffin, IV et al. |
| 6,206,830 B1 | 3/2001 | Diab et al. |

(56) References Cited

U.S. PATENT DOCUMENTS

| | | |
|---|---|---|
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,294,062 B1 | 9/2001 | Buck, Jr. et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,425,863 B1 | 7/2002 | Werner et al. |
| 6,430,437 B1 | 8/2002 | Marro |
| 6,430,525 B1 | 8/2002 | Weber et al. |
| 6,443,881 B1 | 9/2002 | Finger |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,216 B1 | 4/2003 | Wilsey et al. |
| 6,541,756 B2 | 4/2003 | Schulz et al. |
| 6,542,764 B1 | 4/2003 | Al-Ali et al. |
| 6,544,212 B2 | 4/2003 | Galley et al. |
| 6,556,853 B1 | 4/2003 | Cabib et al. |
| 6,572,566 B2 | 6/2003 | Effenhauser |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,554 B1 | 3/2004 | Miltner et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,073 B1 | 4/2004 | Motamedi et al. |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,780,651 B2 | 8/2004 | Douglas et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,337 B2 | 12/2004 | Cornsweet |
| 6,837,337 B2 | 1/2005 | Thomas et al. |
| 6,847,449 B2 | 1/2005 | Bashkansky et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,020,506 B2 | 3/2006 | Fine et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,190,464 B2 | 3/2007 | Alphonse |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,280,860 B2 | 10/2007 | Ikeda et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,734 B2 | 12/2007 | Dogariu |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,353,055 B2 | 4/2008 | Hogan |

(56) References Cited

U.S. PATENT DOCUMENTS

| | | |
|---|---|---|
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,557,929 B2 | 7/2009 | Fang-Yen et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,884,945 B2 | 2/2011 | Srinivasan et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,168 B2 | 7/2012 | Lowery |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |

(56) References Cited

U.S. PATENT DOCUMENTS

| | | | |
|---|---|---|---|
| 8,489,364 | B2 | 7/2013 | Weber et al. |
| 8,498,684 | B2 | 7/2013 | Weber et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 2002/0016533 | A1 | 2/2002 | Marchitto et al. |
| 2005/0043597 | A1 | 2/2005 | Xie |
| 2005/0070771 | A1 | 3/2005 | Rule et al. |
| 2006/0063988 | A1 | 3/2006 | Schurman et al. |
| 2006/0187462 | A1 | 8/2006 | Srinivasan |
| 2009/0299157 | A1 | 12/2009 | Telfort et al. |
| 2010/0261979 | A1 | 10/2010 | Kiani |
| 2011/0015505 | A1 | 1/2011 | Schurman et al. |
| 2011/0209915 | A1 | 9/2011 | Telfort et al. |
| 2011/0319731 | A1 | 12/2011 | Schurman et al. |
| 2012/0116175 | A1 | 5/2012 | Al-Ali et al. |
| 2012/0265039 | A1 | 10/2012 | Kiani |
| 2012/0286955 | A1 | 11/2012 | Welch et al. |
| 2013/0060108 | A1 | 3/2013 | Schurman et al. |
| 2013/0109935 | A1 | 5/2013 | Al-Ali et al. |
| 2013/0162433 | A1 | 6/2013 | Muhsin et al. |
| 2013/0274571 | A1 | 10/2013 | Diab et al. |
| 2014/0025306 | A1 | 1/2014 | Weber et al. |
| 2014/0051954 | A1 | 2/2014 | Al-Ali et al. |
| 2014/0125495 | A1 | 5/2014 | Al-Ali |
| 2014/0128696 | A1 | 5/2014 | Al-Ali |
| 2014/0128699 | A1 | 5/2014 | Al-Ali et al. |
| 2014/0142402 | A1 | 5/2014 | Al-Ali et al. |
| 2014/0200420 | A1 | 7/2014 | Al-Ali |
| 2014/0200422 | A1 | 7/2014 | Weber et al. |
| 2014/0296664 | A1 | 10/2014 | Bruinsma et al. |
| 2014/0309506 | A1 | 10/2014 | Lamego et al. |
| 2014/0309559 | A1 | 10/2014 | Telfort et al. |

FOREIGN PATENT DOCUMENTS

| | | |
|---|---|---|
| EP | 0127947 | 8/1990 |
| EP | 0280986 | 7/1992 |
| EP | 0317121 | 2/1994 |
| EP | 0536187 | 9/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |
| WO | WO 95/32416 | 11/1995 |
| WO | WO 02/065090 | 8/2002 |

OTHER PUBLICATIONS

Arnold, V.W. et al., "Fourier Transformation Infrared Spectrometry—A New (Old) Method of Detection in Forensic Chemistry and Criminal Investigation," Beitr Gerichtl Med. 47:123-47 (1989).

Bruulsema, J.T. et al., "Correlation Between Blood Glucose Concentration in Diabetics and Noninvasively Measured Tissue Optical Scattering Coefficient," Opt. Lett. 22(3):190-93 (1997).

Burritt, M.F., "Current Analytical Approaches to Measuring Blood Analytes," Clin. Chem. 36(8 pt.2):1562-66 (1990).

Chira, I.S. et al., "Light Scattering by Blood Components After Supplying Glucose," Biomed. Tech. 35(5): 102-06 (1990).

Christison, G.B. et al., "Laser Photoacoustic Determination of Physiological Glucose Concentrations in Human Whole Blood," Med. Biol. Eng. Comput. 31(3):284-90 (1993).

Cote, G.L. et al., "Noninvasive Optical Polarimetric Glucose Sensing Using a True Phase Measurement Technique," IEEE Trans. Biomed. Enq, 39(7):752-56 (1992).

CRC Press, "Handbook of Chemistry and Physics" 64th ed. pp. D-223, D-224, and D. 235.

Drezek, R. et al., "Light Scattering From Cell: Finite Difference Time-Domain Simulations and Goniometric Measurements," Appl. Opt. 38(16):3651-61 (1999).

Duck, F. A., Physical Properties of Tissue, (Academic London 1990).

Dyer, D.G. et al., "Accumulation of Maillard Reaction Products in Skin Collagen in Diabetes and Aging," J. Clin. Invest. 91:2463-69 (1993).

Esenaliev, R.O, et al., "Noninvasive Monitoring of Glucose Concentration with Optical Coherence Tomography," Optics Lett. 26(13):992-94 (2001).

Faber, D.J. et al., "Light Absorption of (oxy-)Hemoglobin Assessed by Spectroscopic Optical Coherence Tomography," Optics Lett. 28(16):1436-38 (2003).

Fercher, A. et al., "In Vivo Optical Coherence Tomography," Amer, J. Opthalmol, 116(1):113-14 (1993).

Flock, S.T. et al., "Total Attenuation Coefficients and Scattering Phase Functions of Tissues and Phantom Materials at 633 nm," Med. Phvs. 14(5):835-41 (1987).

Fogt, E.J., "Continuous Ex Vivo and In Vivo Monitoring with Chemical Sensors," Clin. Chem. 36(8 pt.2):1573-80 (1990).

Frank, K.H. et al., "Measurements of Angular Distributions of Rayleigh and Mie Scattering Events in Biological Models," Phvs. Med. Biol. 34(8):1901-16 (1989).

Gabriely.I. et al., "Transcutaneous Glucose Measurement Using Near-Infrared Spectroscopy During Hypoglycemia," Diabetes Care 22(12):2026-32 (1999).

Galanzha, E.I. et al., "Skin Backreflectance and Microvascular System Functioning at the Action of Osmotic Agents," J, Phvs. D. Appl. Phvs. 36:1739-46 (2003).

Gilbert, J.W. et al., "A Cerebrospinal Fluid Glucose Biosensor for Diabetes Mellitus," ASAIO J. 38(2):82-87 (1992).

Goetz, M.J. et al., "Application of a Multivariate Technique to Raman Spectra for Quantification of Body Chemicals," IEEE Trans, Biomed. Eng, 42:728-31 (1995).

Goodman, J.W., Some Fundamental Properties of Speckle, J. Optical Soc. of America 66(11):1145-50 (1976).

Gough, D.A., "The Composition and Optical Rotary Dispersion of Bovine Aqueous Humor," Diabetes Care 5(3):266-70 (1982).

Gunby, P., "Laser-Implant Contact Lens Could be Glucose Monitor," JAMA 243(4):317 (1980).

Guyton, A.C., Textbook of medical physiology, (W.B. Saunders Company 1992).

Huang, D, et al., "Optical Coherence Tomograph," Science 254:1178-81 (1991).

Huang, Y.L. et al., "On-Line Determination of Glucose Concentration Throughout Animal Cell Cultures Based on Chemiluminescent Detection of Hydrogen Peroxide Coupled with Flow-Injection Analysis," J. Biotechnol. 18(1-2):161-72 (1991).

International Search Report from PCT/US05/26744, mailed Oct. 25, 2006.

International Search Report, from corresponding PCT/US06/13775, mailed Sep. 13, 2006.

International Search Report, from corresponding PCT/US06/21535, mailed Feb. 21, 2008.

Kaiser, N., "Laser Absorption Spectroscopy with an ATR Prism—Noninvasive in Vivo Determination of Glucose," Horm. Metab. Res. Suppl. 8:30-33 (1979).

(56) References Cited

OTHER PUBLICATIONS

Kajiwara, K. et al., "Spectroscopic Quantitative Analysis of Blood Glucose by Fourier Transform Infrared Spectroscopy with an Attenuated Total Reflection Prism," Med, Prog. Technol. 18(3):181-89 (1992).

Khalil, O.S. "Spectroscopic and Clinical Aspects of Noninvasive Glucose Measurements," Clin. Chem. 45(2):165-77 (1999).

Kholodnykh, A.I. et al., "Precision of Measurement of Tissue Optical Properties with Optical Coherence Tomography," Appl. Optics 42(16):3027-37 (2003).

King, T.W. et al., "Multispectral Polarimetric Glucose Detection Using a Single Pockels Cell," Optical Engineering 33(8):2746-53 (1994).

Kohl, M. et al., "The Influence of Glucose Concentration Upon the Transport of Light in Tissue-Simulating Phantoms," Phvs. Med. Biol. 40:1267-87(1995).

Kohl, M. et al., "Influence of Glucose Concentration on Light Scattering in Tissue-Simulating Phantoms," Optics Letters 19(24):2170-72 (1994).

Kruse-Jarres, J.D., "Physicochemical Determinations of Glucose in Vivo," J. Clin. Chem. Clin. Biochem. 26(4):201-08 (1988).

Larin, K.V. et al., "Optoacoustic Signal Profiles for Monitoring Glucose Concentration in Turbid Media," SPIE Proc. 3726:576-83 (1988).

Larin, K.V. et al., "Noninvasive Blood Glucose Monitoring With Optical CoherenceTomography," Diabetes Care 25(12):2263-67 (2002).

Larin, K.V. et al., "Specificity of Noninvasive Blood Glucose Sensing Using Optical Coherence Tomography Technique: A Pilot Study," Physics in Med. & Biol. 48:1371-90 (2003).

Larin, K.V. et al., "Phase-Sensitive Optical Low-Coherence Reflectometry for the Detection of Analyte Concentrations," Appl. Optics 43(17):3408-14 (2004).

Lide, D.R., CRC Handbook of Chemistry and Physics, $79^{th}$ ed. (CRC Press, Boca Raton, Florida, 1998).

MacKenzie, H.A. et al., "Advances in Photoacoustic Noninvasive Glucose Testing," Clin. Chem. 45(9):1587-95 (1999).

Maier, J.S. et al., "Possible Correlation Between Blood Glucose Concentration and the Reduced Scattering Coefficient of Tissues in the Near Infrared," Optics Lett. 19(24):2062-64 (1994).

March, W. et al., "Optical Monitor of Glucose," Trans. Am. Soc. Artlf. Intern. Organs 25:28-31 (1979).

March, W.F. et al., "Noninvasive Glucose Monitoring of the Aqueous Humor of the Eye: Part II. Animal Studies and the Scleral Lens," Diabetes Care 5(3):259-65 (1982).

Mendelson, Y. et al., "Blood Glucose Measurement by Multiple Attenuated Total Reflection and Infrared Absorption Spectroscopy," IEEE Trans. Biomed. Eng. 37(5):458-65 (1990).

Moreno-Bondi, M,C. et al., "Oxygen Optrode for Use in a Fiber-Optic Glucose Biosensor," Anal. Chem. 62(21):2377-80 (1990).

Muller, A., "In Vivo Measurement of Glucose Concentration with Lasers," Harm. Metab. Res. Suppl. 8:33-35 (1979).

Narayanaswamy, R., "Current Developments in Optical Biochemical Sensors," Biosens. Bioelectron. 6(6):467-75 (1991).

Pan, S. et al., "Near-Infrared Spectroscopic Measurement of Physiological Glucose Levels in Variable Matrices of Protein and Triglycerides," Anal, Chem. 68:1124-35 (1996).

Peterson, J.I. et al., "A Miniature Fiberoptic pH Sensor Potentially Suitable for Glucose Measurements," Diabetes Care 5(3):272-74 (1982).

Quan, K.M. et al., "Glucose Determination by a Pulsed Photoacoustic Technique—An Experimental Study Using a Gelatin-Based Tissue Phantom," Phys. Med. Biol. 38(12): 1911-22 (1993).

Rabinovitch, B. et al., "Noninvasive Glucose Monitoring of the Aqueous Humor of the Eye: Part I. Measurement of Very Small Optical Rotations," Diabetes Care 5(3):254-58 (1982).

Robinson, M.R. et al., "Noninvasive Glucose Monitoring in Diabetic Patients: A Preliminary Evaluation," Clin. Chem. 38(9):1618-22 (1992).

Robinson, R.J, et al., "Glucose-Sensitive Membrane and Infrared Absorption Spectroscopy for Potential Use as an Implantable Glucose Sensor," ASAIO J. 38(3):M458-62 (1992).

Rusch, T.L. et al., "Signal Processing Methods for Pulse Oximetry," Comput. Biol. Med. 26(2):143-59 (1996).

Schmitt, J.M. et al., "Measurement of Optical Properties of Biological Tissues by Low-Coherence Reflectometrv," Appl. Optics 32(30):6032-42 (1993).

Schmitt, J.M. et al., "Optical Coherence Tomography (OCT): A Review," IEEE J. Selected Topics in Quantum Electronics 5(4):1205-15 (1999).

Schmitt, J.M. et al., "Speckle in Optical Coherence Tomography," J. Biomed. Optics 4(1 ):95-105 (1999).

Sevick, E.M. et al., "Near-Infrared Optical Imaging of Tissue Phantoms with Measurement in the Change of Optical Path Lengths," Adv. Exp. Med. Biol. 345:815-23 (1994).

Sodickson, L.A. et al., "Kromoscopic Analysis: A Possible Alternative to Spectroscopic Analysis for Noninvasive Measurement of Analytes in Vivo," Clin. Chem. 40(9):1838-44 (1994).

Star, W.M. et al., "Light Dosimetry: Status and Prospects," J. Photochem. Photobiol. 1(2):149-67 (1987).

Stoddart, S. et al., "Pulse Oximetry: What it is and How to Use it," J. Neonatal Nursing 10:12-14 (1997).

Takai, N. et al., "Studies of the Development of Optical Fiber Sensors for Biochemical Analysis," Artif. Organs 15{2):86-89 (1991).

Tunchin, V.V. et al., "Light Propagation in Tissues with Controlled Optical Properties," J. Biomed. Opt. 2(4):401-17 (1997).

Wang, L. et al., "Speckle Reduction in Laser Projection Systems by Diffractive Optical Elements," Appl. Optics 37(10):1770-75 (1998).

Weast, R.C., et al, CRC Handbook of Chemistry and Physics, $70^{th}$ ed., (CRC Cleveland, Ohio, 1989).

Welch, A.J. et al., Practical Models for Light Distribution in Laser-Irradiated Tissue, Lasers Surq. Med. 6(6):488-93 (1987).

Wicksted, J.P. et al., "Monitoring of Aqueous Humor Metabolites Using Raman Spectroscopy," SPIE Proc. 2135:264-74 (1994).

Zeller, H. et al., Blood Glucose Measurement by Infrared Spectroscopy,• J. Artif. Organs 12(2):129-35 (1989).

Zhao, Yonghua, et al. "Doppler standard deviation imaging for clininal monitoring of in vitro human skin blood flow." Optics Letters. Sep. 15, 2000. vol. 25, No. 18 pp. 1358-1360.

Ruth, Bernhard, et al. "Noncontact determination of skin blood flow using the laser speckle method: Application to patients with peripheral arterial occlusive disease (PAOD) and to type-1 diabetics." 1993. Wiley-Liss. Lasers in Surgery and Medicine. 13: 179-188.

NONINVASIVELY MEASURING ANALYTE LEVELS IN A SUBJECT

CROSS-REFERENCE TO RELATED APPLICATIONS

This application is a continuation of U.S. application Ser. No. 13/229,410 entitled "Methods for Noninvasively Measuring Analyte Levels in a Subject" filed Sep. 9, 2011, which is a continuation of U.S. application Ser. No. 11/445,631 entitled "Methods for Noninvasively Measuring Analyte Levels in a Subject" filed Jun. 2, 2006, which claims the benefit of U.S. Provisional Application No. 60/686,721 entitled "Method for Noninvasively Measuring Blood Glucose" filed Jun. 2, 2005, and is a continuation-in-part of U.S. application Ser. No. 10/916,236, entitled "Method And Apparatus For Monitoring Glucose Levels In A Biological Tissue," filed Aug. 11, 2004. All of the above referenced applications are hereby incorporated by reference in their entirety herein. This application is also related to U.S. Provisional Application No. 60/671,285, entitled "Method For Data Reduction And Calibration Of An OCT-Based Blood Glucose Monitor," filed Apr. 14, 2005, the entire contents of which is herein incorporated by reference.

BACKGROUND OF THE INVENTION

1. Field of the Invention

The present invention relates generally to methods for noninvasively measuring blood glucose or other analyte levels in a subject by measuring localized changes in light scattering from skin or other biological tissue. For example, such a method can include identifying tissue structures where the effect of blood glucose concentrations or levels are high, and targeting localized regions within the identified structures to measure blood glucose concentrations.

2. Description of the Related Art

Monitoring of blood glucose (blood sugar) levels has long been critical to the treatment of diabetes in humans. Current blood glucose monitors employ a chemical reaction between blood serum and a test strip, requiring an invasive extraction of blood via a lancet or pinprick to the finger. Although small handheld monitors have been developed to enable a patient to perform this procedure anywhere, at any time, the inconvenience associated with this procedure—specifically the blood extraction and the need for test strips—has led to a low level of compliance by diabetic patients. Such low compliance can lead to diabetic complications. Thus, a non-invasive method for monitoring blood glucose is needed.

Studies have shown that optical methods can be used to detect small changes in light scattering from biological tissue related to changes in levels of blood sugar. Although highly complex, a first order approximation of transmitting monochromatic light through biological tissue can be described by the following simplified equation:

$$I_R = I_0 \exp[-(\mu_a + \mu_s)L],$$

where $I_R$ is the intensity of light reflected from the skin, $I_0$ is the intensity of the light illuminating the skin, $\mu_a$ is the absorption coefficient of the skin at the specific wavelength of the light, $\mu_s$ is the scattering coefficient of the skin at the specific wavelength of the light, and L is the total path traversed by the light. From this relationship, it can be seen that the intensity of the reflected light decays exponentially as either the absorption or the scattering by the tissue increases. The attenuation of light can be characterized by an attenuation coefficient, which is the sum of $\mu_s$ and $\mu_a$.

It is well established that there is a difference in the index of refraction between blood serum/interstitial fluid (IF) and cell membranes (such as membranes of blood cells and skin cells). (See, R. C. Weast, ed., CRC Handbook of Chemistry and Physics, 70th ed., (CRC Cleveland, Ohio 1989).) This difference can produce characteristic scattering of transmitted light. Glucose, in its varying forms, is a major constituent of blood and IF. The variation in glucose levels in either blood or IF changes the refractive index of blood-perfused tissue, and thus the characteristic of scattering from such tissue. Further, glucose-induced changes to the refractive index are substantially greater than changes induced by variation of concentrations of other osmolytes in physiologically relevant ranges. In the near-infrared (NIR) wavelength range, blood glucose changes the scattering coefficient, $\mu_s$, more than it changes the absorption coefficient, $\mu_a$. Thus, optical scattering of the blood/IF and cell combination varies as the blood glucose level changes. Accordingly, there is the potential for non-invasive measurement of blood glucose levels.

Current non-invasive optical techniques being explored for blood glucose applications include polarimetry, Raman spectroscopy, near-infrared absorption, scattering spectroscopy, photoacoustics, and optoacoustics. Despite significant efforts, these techniques have shortcomings, such as low sensitivity (signal-to-noise ratio) for the glucose concentrations at clinically-relevant levels, low accuracy (less than that of current invasive home monitors), and insufficient specificity of glucose level measurement within a relevant physiological range of 1.7-27.8 mM/L or 30-500 (mg/dL). For example, diffuse reflectance, or diffuse scattering, has been explored as a technique for noninvasively measuring levels of blood glucose. M. Kohl, Optics Letters, 19(24) 2170-72 (1994); J. S. Maier, et al., Optics Letters, 19(24) 2062-64 (1994). Using diffuse reflectance, a glucose-induced change of around 0.2%-0.3% in the scattering coefficient per 18 mg/dL (or 1 mM/L) has been measured. This measured change is too small to be utilized efficiently for a blood-glucose monitor for home use. Additionally, glucose-induced changes to the scattering coefficient can be masked by changes induced by temperature, hydration, and/or other osmolytes. Accordingly, there is a need for a method to conveniently, accurately, and non-invasively monitor glucose levels in blood.

Optical coherence tomography, or OCT, is an optical imaging technique that uses light waves to produce high-resolution imagery of biological tissue. OCT produces images by interferometrically scanning, in depth, a linear succession of spots and measuring absorption and/or scattering at different depths at each successive spot. The data then is processed to present an image of the linear cross section. The key benefits of such a system in imaging applications include the ability to achieve a high resolution, e.g., better than 10 micrometers, and the ability to select the depth at which a sample can be imaged. For example, blood vessels beneath the surface of the skin can be imaged using such a system.

As discussed in U.S. application Ser. No. 10/916,236, and in R. O. Esenaliev, et al., Optics Letters, 26(13) 992-94 (2001), the entire disclosure of which is incorporated by reference, it has been proposed that OCT might be useful in measuring blood glucose. However, difficulties associated with this technique include the large number of scans required to reduce optical noise, or speckle, which arises from wavefront distortion when coherent light scatters from tissue. While an OCT imaging system can reduce speckle by averaging it out over many scans or measurements, this approach is time-consuming, which makes the use of a conventional OCT imaging system impractical for in-home monitoring of blood glucose levels. Additionally, an OCT imaging system requires complex processing to form a workable image and to analyze the image data sufficiently in order to determine glucose levels.

Accordingly, there is a need for enhanced OCT systems for measuring analytes such as blood glucose levels.

SUMMARY OF THE INVENTION

In accordance with the present invention, a method for non-invasively measuring glucose levels in blood is presented. Specifically, changes in a scattering profile produced from an OCT-based monitor are related to changes in blood glucose levels by focusing on highly localized regions of the scattering profile where changes to the scattering profile induced by temperature, hydration, and other osmolytes are negligible. Glucose-induced changes to the scattering coefficient measured from these localized regions range between about 2% and about 20% per 1 mM/L or 18 mg/dL, with an average value of about 12% per 18 mg/dL. These percentage values are significantly higher than those measured using other methods. Additionally, within the localized regions, effects to the scattering coefficient induced by temperature, hydration, and other osmolytes are negligible compared to the effects of glucose, and, accordingly, can be ignored. The changes in the scattering profile can be related to changes in glucose concentrations by one or more mathematical algorithms.

A method for noninvasively measuring blood glucose-levels in biological tissue is described herein. The method includes the steps of scanning a two-dimensional area of skin with a monitor based on non-imaging optical coherence tomography, collecting cross-sectional depth measurement data continuously during the scanning step, and identifying at least one localized region within the cross-sectional depth measurement data, wherein the at least one localized region corresponds to a structure within the skin where glucose-induced changes to the cross-sectional depth measurement data are prominent. Further, the method includes the step of relating the cross-sectional depth measurement data to blood glucose levels.

In one exemplary embodiment, a method for calibrating OCT measurements using multiple light wavelengths is described to identify a tissue for measurement. At least two OCT scattering profiles can be obtained from light attenuated by a subject's tissue as a function of tissue depth. Non-limiting types of tissue include vascular tissue (e.g., a blood vessel wall), at least one component of blood, dermal tissue surrounding the vascular tissue, or some combination of the aforementioned types. The OCT scattering profiles can be obtained at different wavelengths of light such that the tissue can exhibit a different attenuation coefficient for each wavelength. The attenuation of light can be based at least in part on the presence of an analyte associated with the tissue (e.g., water or hemoglobin). The wavelengths can also be chosen such that the tissue has a different absorption coefficient at the two wavelengths. The wavelengths can also be chosen such that the scattering coefficient is larger than the absorption coefficient at the first selected wavelength, and optionally the absorption coefficient at the second wavelength is larger than the absorption coefficient at the first wavelength. A localized region (e.g., one or more depths) can be identified corresponding to a tissue location of OCT measurement calibration. Such calibration can be based upon a differential comparison of the two OCT scattering profiles. A blood glucose measurement (e.g., some type of chemical blood analysis measurement) can be associated with each of the OCT scattering profiles for calibrating other OCT measurements (e.g., using the OCT scattering profiles and blood glucose measurements to make a calibration between attenuation coefficient and blood glucose concentration). In general, the localized region can have changing light attenuation coefficients based on the presence of blood glucose or other measurable analytes.

With respect to the exemplary method previously described, the OCT scattering profiles can be normalized prior to differential comparison, with a depth corresponding to a tissue location for OCT measurement calibration depending upon a differential comparison of normalized OCT profiles (e.g., subtracting one normalized profile from another at corresponding depth locations). Normalization can be performed by dividing the scattering data of a respective OCT profile by the profile's respective peak intensity value. One or more extrema points in the differential comparison of normalized OCT profiles can be identified, and subsequently correlated with the depth of the tissue location or some other measure of the localized region corresponding with the tissue location.

In general, an offset location and an interval can define a localized region of an OCT scattering profile that can be correlated with a particular attenuation coefficient. The offset can correspond with a depth of a tissue location, and the interval can be determined from the offset location and the OCT scattering profile. The offset location and interval can be used to define the region of the OCT scattering profile in which a slope measurement can be correlated with the attenuation coefficient (or the scattering coefficient when absorption effects are small).

Another exemplary embodiment is directed to a method of determining an absorption coefficient in OCT measurements using multiple light wavelengths. Two or more OCT scattering profiles can be obtained as a function of subject tissue depth at different wavelengths of light such that the tissue has a larger scattering coefficient than absorption coefficient at a first selected wavelength (e.g., the scattering coefficient being at least about 5 times greater than the absorption coefficient). A scattering coefficient can be determined from the first OCT scattering profile (e.g., by locating a slope in the first OCT scattering profile). An estimate of a scattering coefficient from the second OCT scattering profile can be obtained from the scattering coefficient of the first OCT scattering profile. Such an estimate can be obtained using scattering theory (e.g., Mie scattering). The absorption coefficient of the second OCT scattering profile can be determined using the estimate of the scattering coefficient at the second selected wavelength. A similar method can also be used to determine a scattering coefficient.

Another method consistent with an embodiment of the invention is directed to calibrating OCT measurements using multiple light wavelengths. Two or more OCT measurements can be obtained as a function of time using different wavelengths of light for each measurement. The wavelengths can be chosen such that the tissue has a larger absorption coefficient at a first selected wavelength relative to a second. Such an absorption coefficient can also depend upon the presence of an analyte (e.g., water) in or around the tissue. One wavelength can also be chosen such that the scattering coefficient exceeds the absorption coefficient by at least about a factor of five. A first OCT measurement can be converted into an analyte measurement as a function of time.

The analyte measurement can be used to calibrate a scattering coefficient measurement as a function of time.

BRIEF DESCRIPTION OF THE DRAWINGS

The present invention will be more readily understood from the detailed description of the embodiment(s) presented below considered in conjunction with the attached drawings, of which.

DETAILED DESCRIPTION OF THE PREFERRED EMBODIMENT

Figure 1:
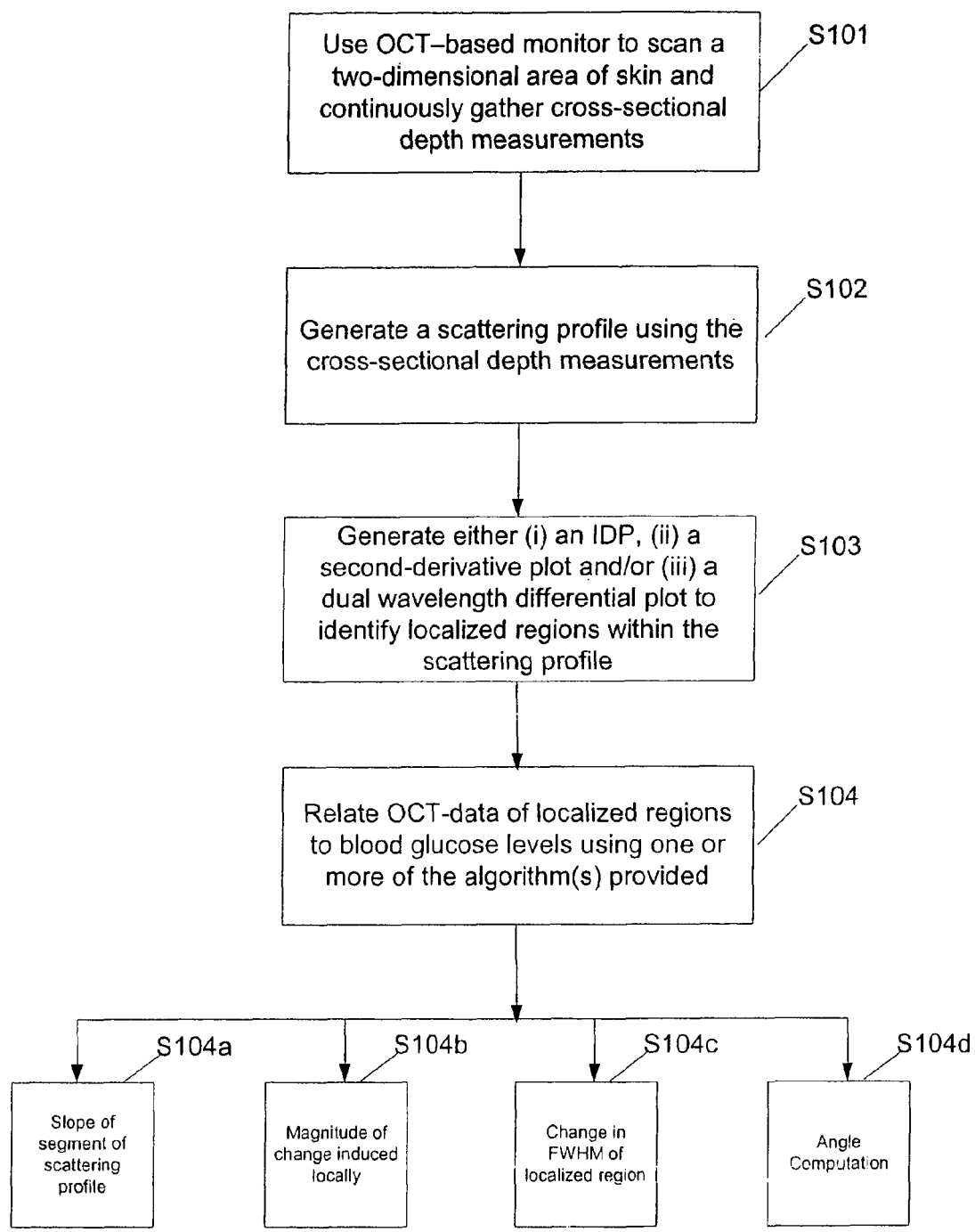
FIG. 1 illustrates a process flow of a method for measuring blood glucose.

According to an embodiment of the present invention, a method for measuring blood glucose levels includes the step of utilizing an OCT-based sensor to take scattering cross-sectional depth measurements on a small area of biological tissue or skin. The OCT-based sensor can be a non-imaging system such as that described in detail in U.S. application Ser. No. 10/916,236. In some embodiments, a two-dimensional area of the skin can be scanned, preferably either in a circular pattern, e.g., with a radius no greater than about 2 mm, or in a filled disk or filled rectangular pattern where the pattern is drawn randomly. As the OCT-based sensor scans the two-dimensional pattern continuously, the sensor continuously collects data corresponding to cross-sectional depth measurements within the biological tissue. Other embodiments can utilize an OCT-based sensor to obtain cross-sectional depth measurements with two-dimensional scanning.

By continuously acquiring a two-dimensional scan pattern and continuously taking cross-sectional depth measurements, the noise associated with OCT sensing, often referred to as "speckle," is reduced more efficiently than scanning tissue using a step-scan method, as described in A. Kholodnykh, et al., *Applied Optics*, 42(16) 3027-37 (2003). In Kholodnykh, a method proposed for an OCT-based system includes scanning a two-dimensional pattern using a step-scan process, where the OCT-based system light beam picks a spot on the skin and takes multiple depth scans. The OCT-based system then averages these depth scans to reduce speckle, and moves on to another spot on the skin, takes multiple depth scans, and averages the depth scans. The OCT-based system repeats this process until a two-dimensional pattern has been made.

In accordance with an embodiment of the present invention, the OCT-based monitor continuously scans an area of skin and continuously collects data. Using this method, fewer scans in less time are required to produce sufficient results. To further reduce speckle, a number of OCT scans can be averaged to produce an average OCT scan result. Thus, data associated with a particular OCT scan at a specific point in time is actually an averaged result of a group of OCT scans.

Using the cross-sectional depth measurements, an intensity profile, or scattering profile, can be generated. Within the scattering profile, localized regions where changes to the scattering profile are dominated by changes in blood glucose can be identified. To locate these regions, a second-derivative plot can be generated, as disclosed in U.S. Provisional Application No. 60/671,285. Using the second-derivative plot, discontinuities in the scattering profile are exaggerated and easily visualized. These discontinuities represent structures in the skin where changes in blood glucose levels dominate the scattering profile. Within these highly localized regions, changes to the scattering profile induced by temperature, hydration, and other osmolytes, such as sodium, potassium, and urea, are very small compared to the effects of glucose, and therefore, can be ignored.

By focusing on the localized regions identified in the intensity profile, there are multiple means that can be used to correlate efficiently the scattering profile to blood glucose levels. Upon identifying these localized regions, the data of the scattering profile can be related to blood glucose levels using one or more mathematical algorithms such as, for example, an algorithm relating the slope of a portion of the OCT data curve to blood glucose levels, where the portion of the OCT data curve corresponds to a discontinuity in the scattering profile. An example of such an algorithm is disclosed in detail in U.S. Provisional Application No. 60/671,285. Optionally, the scattering profile can be related to blood glucose levels by utilizing a magnitude of the glucose-induced localized change, either using a straight peak intensity measurement or using an integrated intensity measurement where each region integrated corresponds to a localized region identified in the second-derivative plot. Alternatively, the scattering profile can be related to blood glucose levels using a change in full width at half-maximum measurement of one or more of the localized regions identified in the second-derivative plot. In addition, the scattering profile can be related to blood glucose levels using an angle computation, where the angle corresponds to a peak change in a localized region and an arbitrary depth.

Another aspect of the embodiment of the present invention includes identifying localized regions of change in the scattering profile by utilizing an intensity difference plot (IDP), which is described in detail in U.S. Provisional Application No. 60/671,285. Although an IDP requires a significant change in glucose concentrations, such as, for example, the change caused by the subject ingesting food during the course of the testing time period while OCT scans are taken, one or more localized regions in the data curve that correspond to tissue structures where noticeable changes to the scattering profile were produced by changes in blood glucose levels can be identified. Once the localized regions are identified, the scattering profile from the localized regions can be related to blood glucose levels using the algorithms mentioned above.

Yet another aspect of the embodiment of the present invention includes using a multiple-wavelength method to identify localized regions of the scattering profile that correspond to tissue and/or tissue structures, such as blood, blood vessels, or other tissue, where changes in the scattering profile due to presence of one or more analytes, such as blood glucose levels, are detectable. The term "wavelength" is used herein to define a region of the electromagnetic radiation spectrum that is distinguishable from other regions. While laser sources with narrow linewidths can be preferable, other lower resolution, or even broadband light sources, can also be used. For example, the invention can be practiced with two wavelengths of light, one of which might be a multimode source spanning several nanometers, e.g., 1308-1312 nm or 1438-1442 nm.

As disclosed in U.S. application Ser. No. 10/916,236, the OCT-based monitor can be constructed such that multiple wavelengths of light are employed to illuminate the skin. Light from multiple wavelengths is absorbed differently by different biological constituents, which differentially reduces the intensity of the scattered light. Moreover, light reflected in and around tissue can be partially absorbed by a constituent for that wavelength. The constituent, in or around the tissue, for that wavelength absorbs some of the light according to the specific wavelength and/or the analyte level in or around the tissue. The differences in the scattering and absorption properties produced by multiple wavelengths interacting with different constituents provide for a determination of an optimal correlation between the scattered signal and a chosen analyte level. For example, light reflection and absorption in and around particular tissues and tissue structures can be correlated with the presence of glucose to provide a measurement of blood glucose levels. Potential tissues and tissue structures, whose light interaction can be correlated with blood glucose levels, include (but are not limited to) vascular tissue (e.g., blood vessel walls), blood and its components (e.g., cells), dermal tissue surround blood vessels, and any combination of the aforementioned tissues and/or tissue structures.

The wavelengths can be chosen to provide an optimal contrast between the absorption and scattering effects of blood and other biological constituents, such as water. For instance, the wavelengths can be chosen to accentuate contrast regarding the presence of a particular analyte that is a signature of the presence of a tissue or tissue structure desired to be targeted by OCT measurements (e.g., water being a signature of the presence of blood perfused tissue). A first wavelength of light emitted from the OCT-based monitor can be chosen such that there is minimum absorption of the light by water compared to the scattering effect, which makes the absorption effects corresponding to water negligible, i.e., the total attenuation coefficient ($\mu_s+\mu_a$) is dominated by the scattering coefficient contribution. In general, when one of the coefficients dominates another in the total attenuation coefficient, we can assume that the less dominant coefficient can be ignored. For example, we can say that $\mu_s \gg \mu_a$ when the scattering coefficient is at least about 5 times, or at least about 10 times, greater than the absorption coefficient. If a second wavelength is chosen to provide peak absorption of light by water, then the difference in light attenuation between the two wavelengths can be used to indicate the position in depth of a blood perfused tissue structure, such as a blood vessel. Clearly, three or more wavelengths of light can also be used to generate corresponding OCT profiles, with specific wavelength pairs utilized in a combination to generate a corresponding light attenuation difference.

According to this aspect of the embodiment of the present invention, OCT scans are taken at two different wavelengths of light, where the first wavelength is chosen such that the scattering effects are dominant over absorption effects of water, and the second wavelength is chosen such that there is substantial absorption by water. Preferably, the scattering data sets produced by scanning a two-dimensional area of the skin by the first and second wavelengths are normalized by finding the peak data point in each scattering data set and dividing all data points by the respective peak data point. Thus, each normalized scattering data set is now a set of decimal values with each peak data point having a value of 1.0.

The normalized scattering data set of the second wavelength can be subtracted from the normalized scattering data set of the first wavelength to produce a differential scattering data set over the depth of the OCT signal, for a specific point in time. As discussed in U.S. Provisional Application No. 60/671,285, there are two variables or parameters associated with fitting the OCT data to blood glucose levels in order to achieve the best correlation. These variables are an offset and an interval. An "offset" is the depth of the OCT data curve at which to begin correlating the OCT data to the blood glucose levels. An "interval" is a certain portion or segment of the OCT data curve that is measured from the offset. For each OCT data curve there are numerous potential combinations or pairs of offsets and intervals. By identifying a peak value in a differential scattering data set, an offset (depth) can be obtained that corresponds to tissue structures where glucose-induced changes are dominant. If a linear fit from the peak value to another data point of the differential data curve is generated, the linear fit corresponds to an offset and interval combination where the slope of the offset and interval combination is highly correlated to blood glucose levels, i.e., the offset and interval can define the localized region of an OCT data curve in which an appropriate attenuation coefficient can be identified and correlated with a blood glucose level. Thus, each linear fit can identify a localized region where glucose-induced changes to the scattering profile are predominant. In cases where the OCT data curve is generated using a wavelength of light in which $\mu_s \gg \mu_a$, the attenuation coefficient reduces to a scattering coefficient.

As mentioned above, by focusing on these highly localized regions along the scattering profile, structures within the skin can be identified where changes to the scattering profile induced by glucose are high, which allows effects induced by temperature, hydration, and other osmolytes to be ignored.

This method focuses on the relative depths of certain structures within the skin, namely, capillaries where blood vessels are prevalent, and identifies the regions of the depth scan that correlate to these structures where glucose levels are known to fluctuate significantly. By focusing on these highly localized regions of a scattering profile, glucose-induced changes to the scattering coefficient of about 2% to about 20% per 18 mg/dL can be obtained, which is significantly higher than the 0.2%-0.3% obtained using other noninvasive optical scattering methods.

A method for measuring blood glucose levels noninvasively is summarized in the flow chart presented in FIG. 1. According to an embodiment of the present invention, at step S101, a non-imaging OCT-based monitor, or a "sensing" OCT-based monitor, can be utilized to take multiple scattering cross-sectional depth measurements on an area of skin. The OCT-based monitor continuously scans a two-dimensional area of skin, preferably scanning either a circle, a filled disk, or a filled rectangular pattern, where the filled pattern is drawn randomly. As the OCT-based monitor scans the skin, the monitor continuously collects cross-sectional depth measurements. As discussed above, continuously scanning a two-dimensional area of skin while continuously collecting data reduces speckle faster than previously known methods that use an OCT-based monitor. Additionally, fewer scans are required to average out speckle and thus, less time is required to take the scans.

Figure 2:
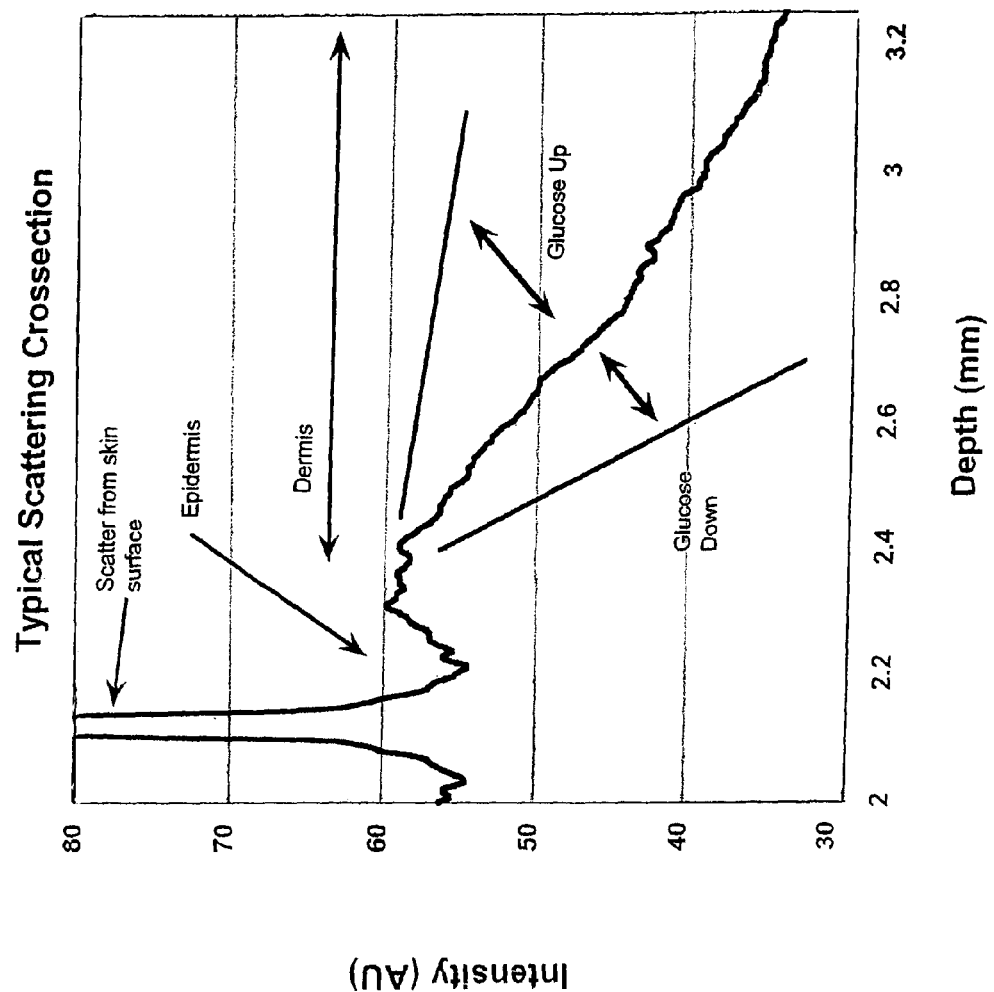
FIG. 2 is a graphical illustration of a typical scattering cross section from a patch of human skin measured using an OCT-based monitor.

At step S102, the cross-sectional depth measurements can be utilized to create a scattering profile in which the OCT data curve is plotted over time. FIG. 2 shows a scattering profile of light scattered from human skin as measured via an OCT-based monitor, according to an embodiment of the present invention. If an appropriate wavelength of light is chosen (e.g., around 1300 nanometers) where "an appropriate wavelength of light" is one in which the absorption coefficient of the light, $\mu_a$, is small relative to the scattering coefficient, $\mu_s$, of the light by the skin. A change in the OCT signal (e.g., a change in the slope of a portion of an OCT profile) likely will be dominated by glucose-induced changes in the tissue scattering. Based on the wavelength of light chosen, the OCT data curve spikes at certain regions of the surface of the skin and then falls dramatically within the epidermis region of the skin. The OCT data curve also rises and slowly decreases within the dermis region as the depth of light in the skin increases. As shown in FIG. 2, the slope of the OCT data curve can increase or decrease relative to the blood glucose level. That is, the slope of the OCT data curve will change in response to glucose level changes in very small defined regions. Because most blood vessels are located in the dermis region, it is this portion of the OCT data curve that provides data for measuring blood glucose levels. To identify this region, one or more of the graphs described below can be generated.

Figure 3:
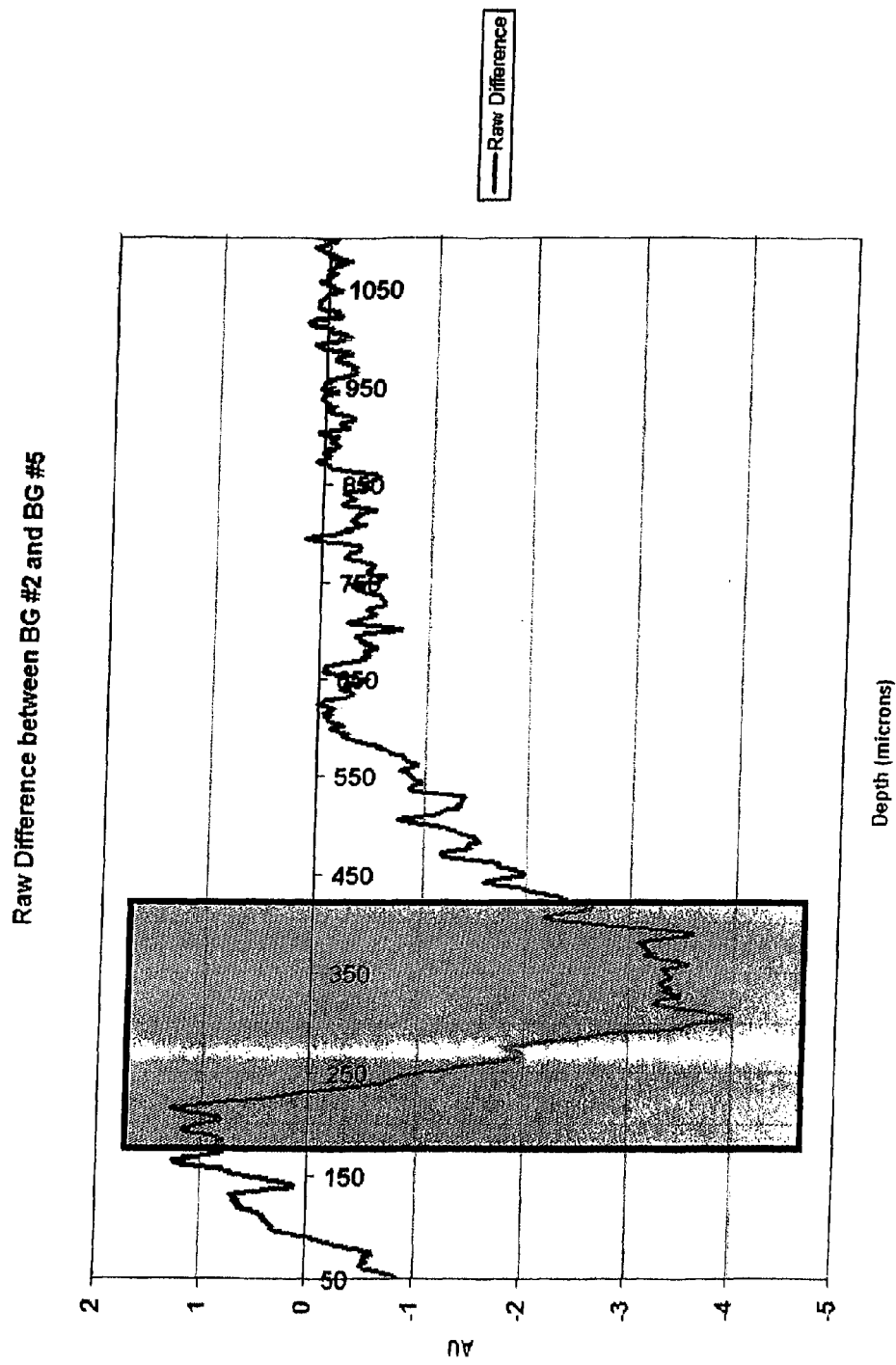
FIG. 3 is an example of an intensity difference plot, according to an embodiment of the present invention.

At step S103, an intensity difference plot (IDP) can be generated to highlight one or more regions of the OCT data curve that correspond to tissue structures where glucose-induced changes are dominant. An example of an intensity difference plot is illustrated in FIG. 3. As described in U.S. Provisional Application 60/671,285, two OCT scans are selected and the difference in the OCT data between the selected two OCT scans is computed. The differential data can then be plotted to produce an IDP, as shown in FIG. 3. From the IDP, one or more zero-crossing points can be identified as well as localized extrema surrounding the zero-crossing points, respectively. The IDP in FIG. 3 has one zero-crossing point, which is located at a depth of about 225 microns. A local maximum data point is located at around 200 microns and a local minimum point is located at around 350 microns. The region of the localized extrema represents a highly localized region where glucose-induced changes to the scattering coefficient are the dominant effect within a tissue structure, and is represented in FIG. 3 by a shaded box. To relate the OCT data to blood glucose levels, the highly localized region can be focused upon and data falling outside this region can be ignored. Within this region, effects due to temperature, hydration, and other osmolytes are negligible. Optionally, the box can be expanded to include potential offsets within a variance amount of the localized extrema. For example, in FIG. 3, the range of potential offsets includes offsets from 175 microns to 400 microns.

According to another aspect of the embodiment, at step S103, the scattering profile can be used to generate a second-derivative plot. As described in U.S. Provisional Application 60/671,285, discontinuities in the scattering profile represent structures in the skin where changes due to variations in blood-glucose levels are high relative to changes in the scattering profile induced by other analytes. The second-derivative plot enhances these discontinuities to help identify one or more highly localized regions where the scattering profile can be related to blood glucose levels.

Figures 4A, 4B:
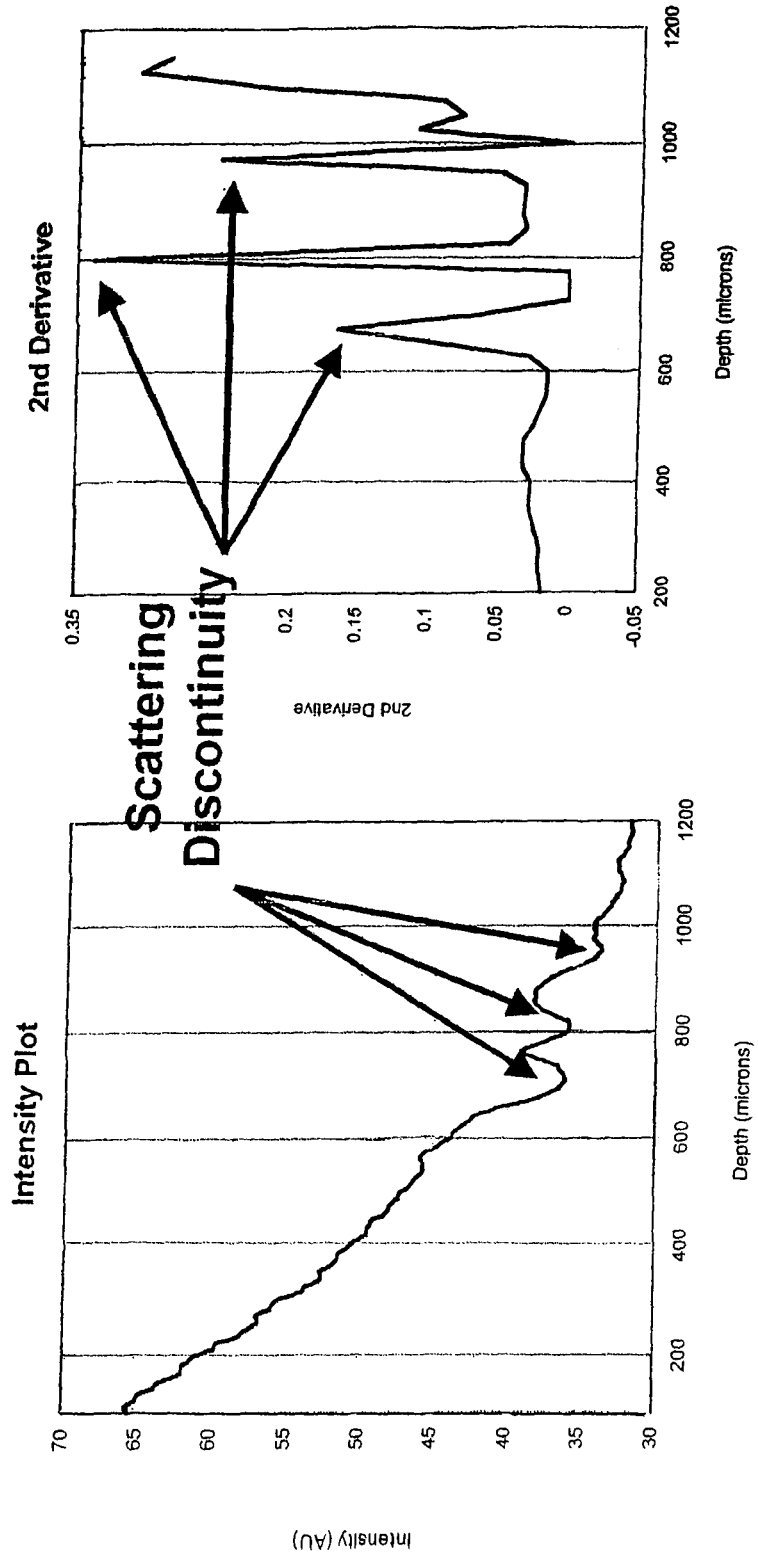
FIGS. 4A and 4B are graphical illustrations in which scattering discontinuities are identified according to an embodiment of the present invention.

FIGS. 4A and 4B graphically illustrate how a second-derivative plot enhances discontinuities in the scattering profile. In FIG. 4A, a scattering profile is plotted against the depth of the scanned area of skin. Discontinuities in the scattering profile are identified by circles in the graph, however, these discontinuities typically are difficult to visualize. In FIG. 4B, a square of a second derivative of the scattering profile is plotted against the depth of the scanned area of skin. The discontinuities in the scattering profile are enhanced by the second derivative computation, while calculating the square value of the second derivative removes any negative values that can exist. The discontinuities correspond to structures in the skin where changes in blood glucose levels are dominant, such as, for example, blood vessels. The scattering data corresponding to the identified localized regions can then be related to blood glucose levels.

Figure 5:
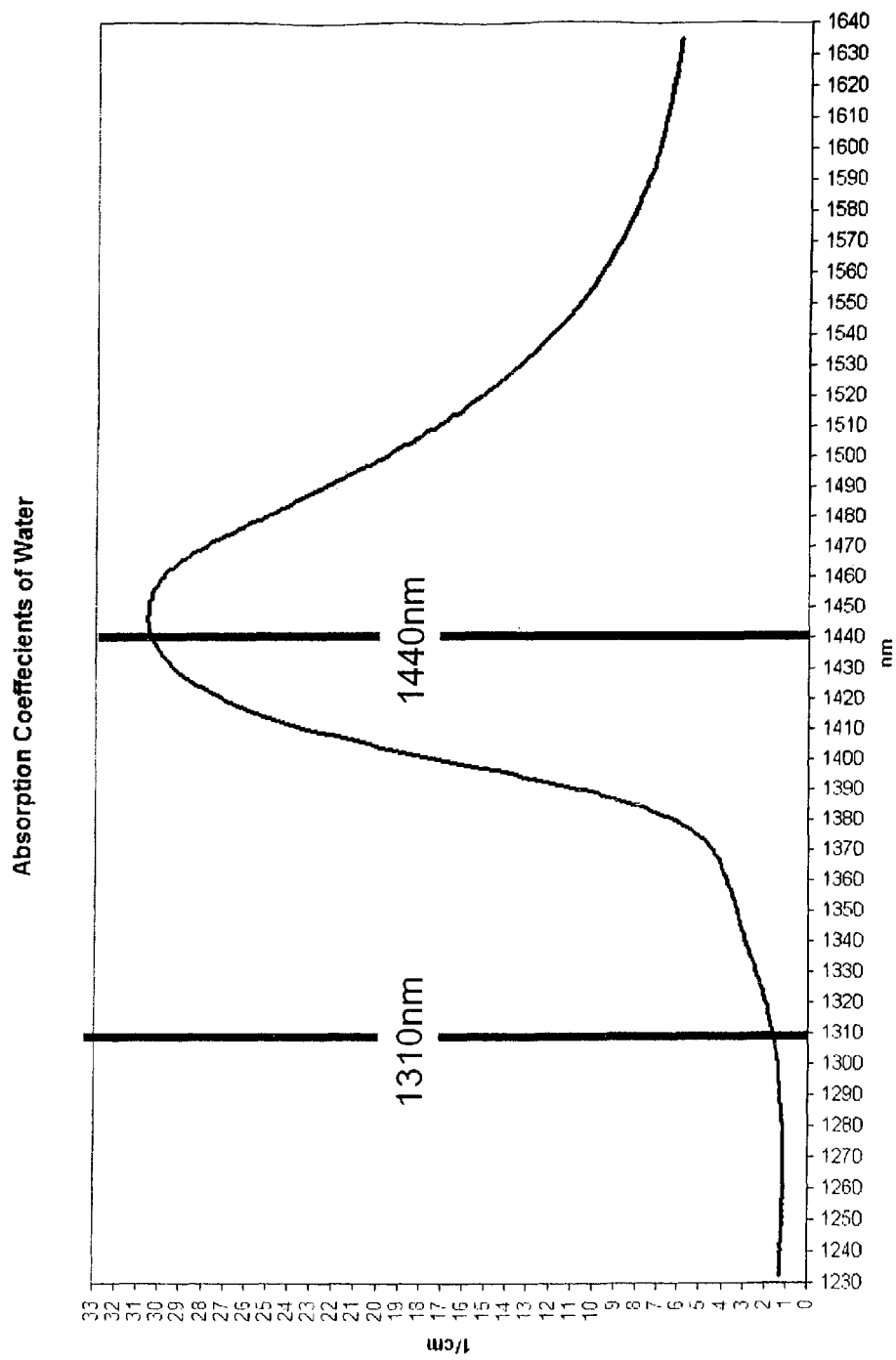
FIG. 5 is a graphical illustration of an absorption effect of water at multiple wavelengths, according to an embodiment of the present invention.

Another aspect of the embodiment includes utilizing multiple wavelengths to identify tissue and/or tissue structures with a high degree of hydration or water content due to blood perfusion, such as blood vessels where changes in blood glucose levels are prevalent, at step S103. The localized regions of the scattering profile that correspond to these tissue structures then correlate well to blood glucose levels. As described above, the OCT-based monitor can utilize multiple wavelengths of light, where one wavelength is chosen that produces a minimum absorption of light by water in the interstitial fluid, and another wavelength is chosen that provides a substantial absorption of light by water. FIG. 5 illustrates the absorption of light by water at different wavelengths. For example, if a first wavelength of light at 1310 nanometers (nm), where the absorption effects of water are minimal, and a second wavelength of light at 1440 nanometers (nm), where the absorption effects of water are maximized, are chosen, the differential scattering data set produced from the OCT data of the two wavelengths can be used to determine tissue structures where hydration is high, such as a blood vessel. Of course, other analytes indicative of a tissue or tissue structure can also be detected by the choice of appropriate light wavelengths. For example, hemoglobin has a peak absorption at 660 nm when deoxygenated and 940 nm when oxygenated. Accordingly, either of these wavelengths can be useful to detect oxygen levels in tissue. It can also be advantageous to select light wavelengths such that the scattering due to the presence of a measured analyte (e.g., blood glucose or hemoglobin) does not differ a great deal in the two wavelengths, i.e., the difference in intensity of the two wavelengths is due mostly to the presence of water or some other analyte indicative of the presence of a blood vessel or other tissue structure.

Figure 6A:
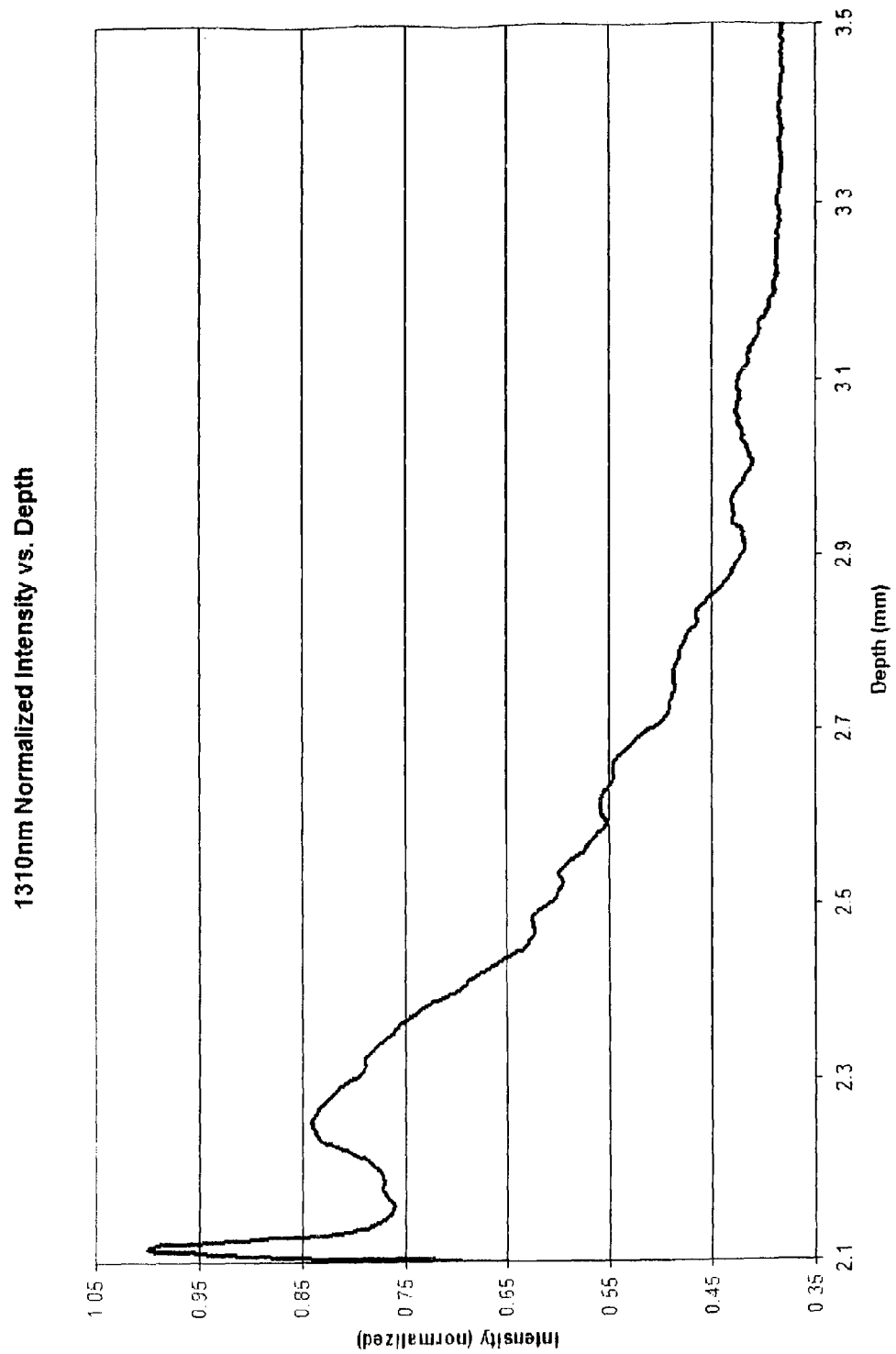
FIGS. 6A and 6B are examples of scattering profiles at wavelengths of 1310 nanometers and 1440 nanometers, respectively, according to an embodiment of the present invention.
Figure 6B:
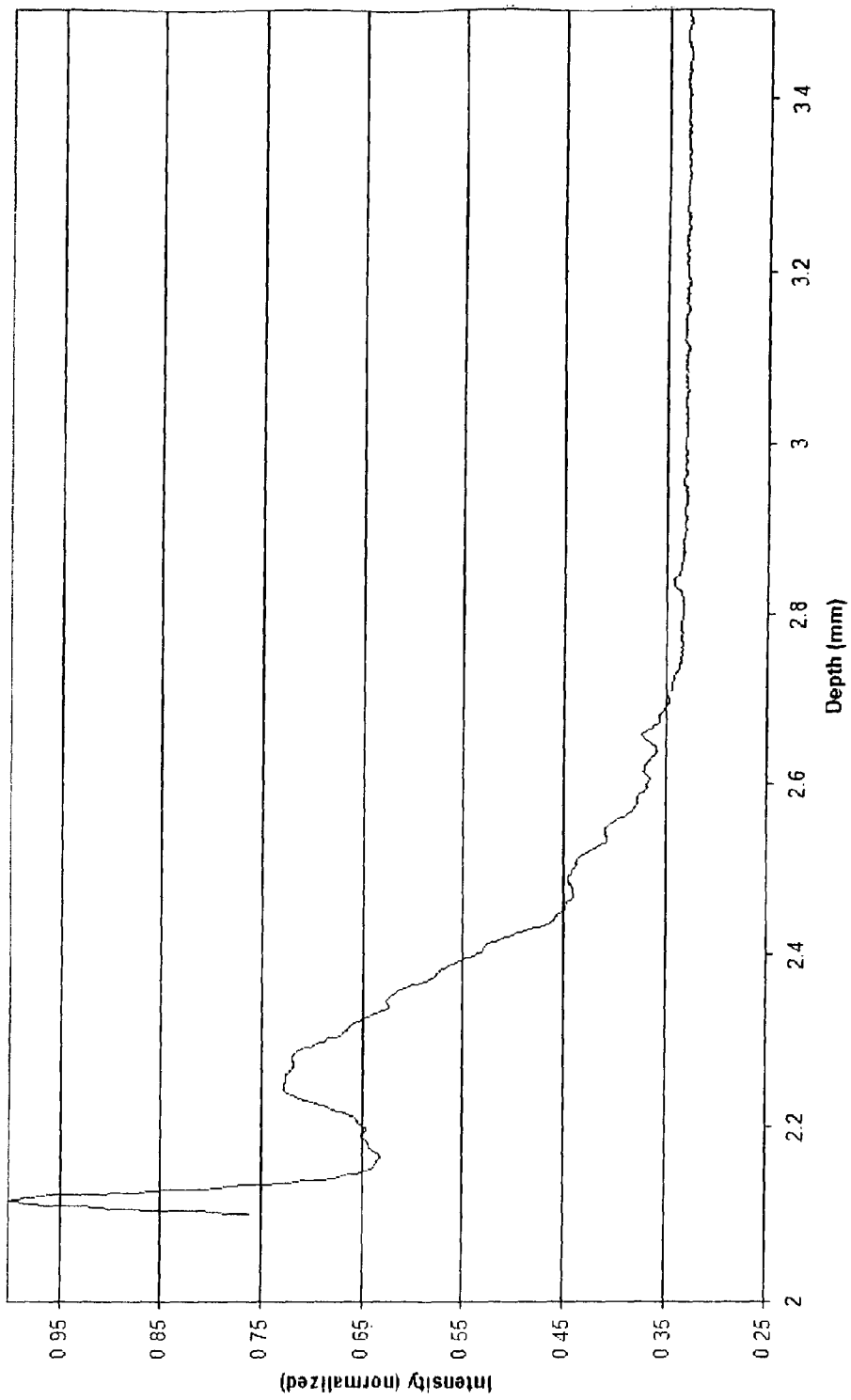

The scattering profiles for each wavelength at a particular point in time can be plotted, as shown in FIGS. 6A and 6B, which represent exemplary scattering profiles for first and second wavelengths of 1310 nm and 1440 nm, respectively. In both FIGS. 6A and 6B, the scattering data set for each wavelength has been normalized using the respective peak intensity value. Thus, the peak intensity value for each scattering data set is 1.0, and each data point around the peak is less than 1.0. Because the sensitivity of the OCT-based monitor is different at the two wavelengths, the scattering profiles of the two wavelengths can not be compared directly. Normalization of the scattering data sets allows direct comparison of the scattering data sets from the two wavelengths.

Figure 7:
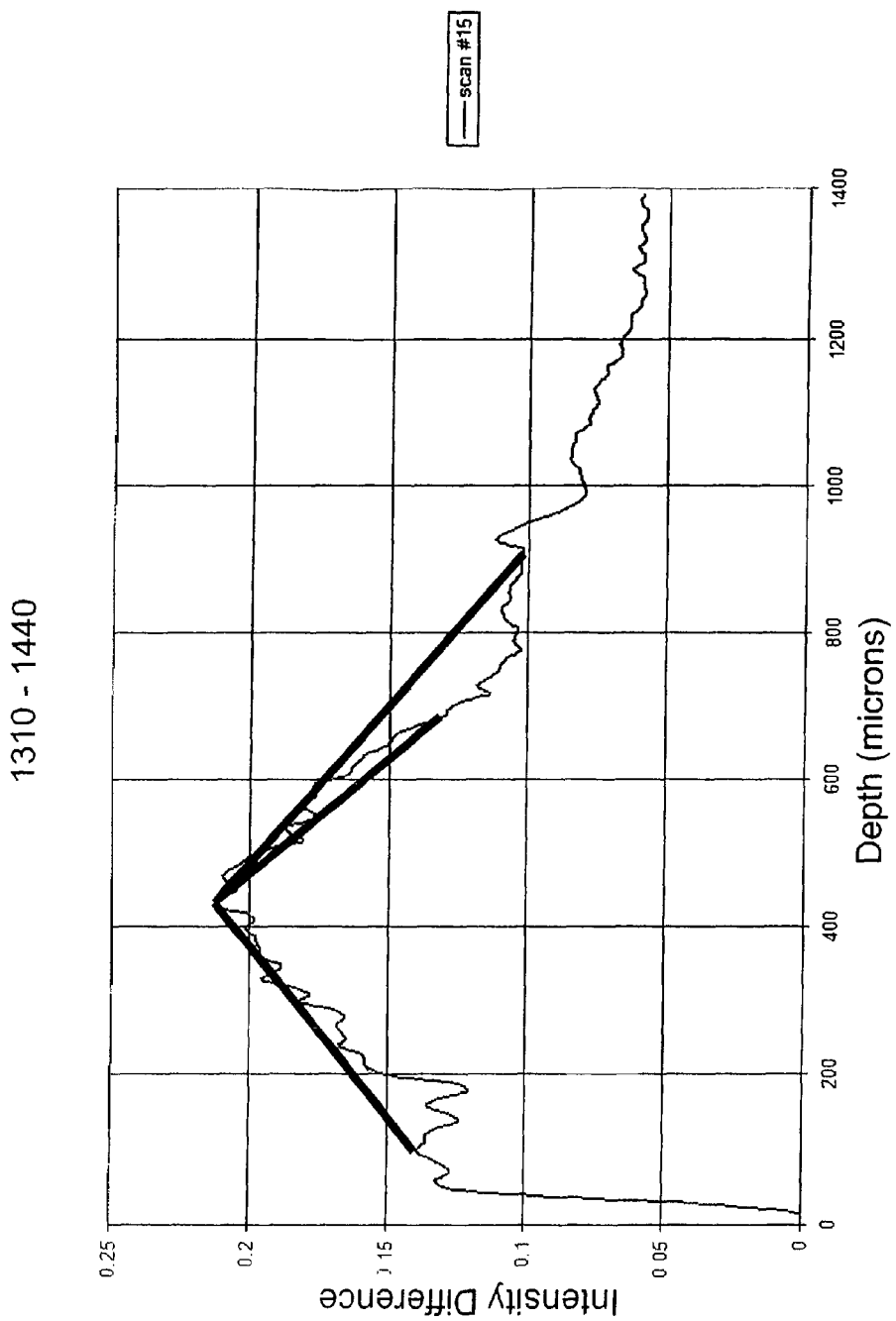
FIG. 7 is a graphical illustration of a differential data set scattering profile, according to an embodiment of the present invention.

Upon normalizing the data, the normalized scattering data set of the second wavelength can be subtracted from the normalized scattering data set of the first wavelength to produce a differential scattering data set. Using the exemplary wavelengths of 1310 nm and 1440 nm, a differential data curve plot can be produced, as shown in FIG. 7. The profile of the differential data curve suggests one or more offset and interval pairs that correspond to localized regions of the scattering profile where variations in blood glucose levels are the predominant effect. One or more peak data points identified in the differential data curve suggests one or more depths or offsets at which to begin correlating the OCT data to blood glucose levels. Using the peak data point(s), one or more intervals can be identified by choosing one or more data points on either side of the peak data point(s). The combination of the offset(s) and the one or more intervals produces offset and interval pairs that can be applied to the scattering profile produced by the first wavelength, e.g., 1310 nm, to identify localized regions where glucose-induced effects to the scattering profile are predominant.

Upon identifying one or more highly localized regions of the scattering profile where glucose-induced changes are prominent, one or more algorithms can be used to relate the scattering profile to blood glucose levels, at step S104. At step S104$a$, the slope of portions or segments of the IDP data curve that correspond to the localized regions can be used to compute predicted blood glucose levels, as described in U.S. Provisional Application 60/671,285. Alternately, at step S104$b$, the scattering profile can be related to blood glucose levels using a magnitude value of a localized change, either using a straight peak intensity measurement or an integrated intensity measurement using the entire localized region. Another option is to use a change in the full-width at half-maximum measurement of one or more of the localized regions, at step S104$c$. Yet another option is to use an angle measurement calculation in relating the OCT data to blood glucose levels.

The description of using multiple wavelengths to locate tissue or tissue structures for glucose monitoring is not intended to limit the use of the technique to the particular application exemplified in the description. Indeed, beyond identifying the presence of water or hydration content of blood vessels, other analytes such as hemoglobin at varying oxygen content can also be utilized as a signature of a particular tissue or tissue structure (e.g., oxygenated tissue). As well, the types of tissue and tissue structures to which multiple wavelength OCT measurements can be used are not limited to blood vessels but can include other vascular tissue, blood (or particular constituents thereof such as cells), dermal tissue surround vascular tissue, and combinations of such exemplary tissues and tissue structures.

Furthermore, the technique is not limited to detecting blood glucose, but can be used to diagnose other conditions unrelated to blood glucose. In one instance, the technique of using of multiple wavelengths to determine tissue hydration levels can be applied in a variety of contexts including assessment and/or monitoring of congestive heart failure, management of fluid therapy for shock or surgery, management of fluid load in dialysis patients (e.g., peritoneal dialysis or hemodialysis), and management of tissue hydration in pulmonary disease and hypertension. For example, multiple wavelength OCT measurements can be used to monitoring clotting factors in blood. Since the scattering coefficient of blood is affected by hydration, use of the multiple wavelengths allows one to determine the contribution to the scattering coefficient that is substantially hydration independent by comparing scattering coefficients at wavelengths that absorb water strongly and weakly. The scattering coefficient at low water absorbing wavelengths can be related to the viscosity, and eventually the clotting factors of the blood. Such a measurement could be useful in post-surgical monitoring of patients who are administered blood thinning agents. The scattering coefficient at low water absorbing wavelengths can also be adjusted using the measurements at higher water absorbing wavelengths. When using any of the calibration methods encompassed by the present application, actual samples of the measured analyte (or other non-chemically oriented types of analyte measurements) can be utilized to aid in calibration (e.g., the use of blood glucose samples as described with reference to glucose monitoring herein).

In a further aspect of the embodiment, multiple wavelength OCT measurements can be utilized to provide an improved estimate of a scattering coefficient or an absorption coefficient from tissue measurements. Such an aspect can be utilized in conjunction with any of the potential applications of the present invention such as determining the viscosity of blood. The following description is with reference to estimating an absorption coefficient, though estimates of a scattering coefficient can also be obtained under analogously consistent conditions.

In one example, a pair of OCT scattering profiles are obtained, each profile corresponding to a measurement at a particular wavelength of light. With reference to the S101 and S102 of the flowchart of FIG. 1 and the corresponding description, the profiles can be obtained by scanning a two-dimensional area of skin to obtain measurements at a number of cross-sectional depths. In this particular example, one profile is obtained using light with a wavelength of about 1310 nm and another profile is obtained using 1440 nm light. The intensity of the reflected light at 1310 nm can be approximated by the following equation:

$$\ln\left(\frac{I_R}{I_O}\right)^{1310} = -L[\mu_s^{1310} + \mu_a^{1310}]$$

where $I_R$ is the reflected light intensity at 1310 nm, $I_o$ is the initial light intensity at 1310 nm, L is the total light pathlength, $\mu_s^{1310}$ is the scattering coefficient of the tissue at 1310 nm, and $\mu_a^{1310}$ is the absorption coefficient of the tissue at 1310 nm.

In some instances, a wavelength can be selected such that one of the scattering or absorption coefficients is stronger than the other to the extent that the contribution of the weaker can be ignored (e.g., when one contribution is at least about 5 times greater or at least about 10 times greater than the other). When measuring hydration levels, the scattering coefficient $\mu_s^{1310}$ is stronger than the absorption coefficient $\mu_a^{1310}$ such that the contribution from $\mu_a^{1310}$ can be ignored; this allows the scattering coefficient $\mu_s^{1310}$ to be determined. Accordingly, a plot of $\ln(I_R/I_o)$ versus depth can yield a line with a slope that can be equated with $\mu_s^{1310}$.

The scattering coefficient at 1310 nm $\mu_s^{1310}$ can be used to provide a measure of the scattering coefficient at 1440 nm, $\mu_s^{1440}$. Various scattering theories, as known to those skilled in the art, can be used to relate the scattering coefficients at the two different wavelengths. For example, under Mie scattering, $(0.7)\mu_s^{1310} \approx \mu_s^{1440}$. Using this estimate for $\mu_s^{1440}$, an estimate of the absorption coefficient at 1440 nm can be found using:

$$\ln\left(\frac{I_R}{I_o}\right)^{1440} = -L[\mu_s^{1440} + \mu_a^{1440}]$$

where $I_R$ is the reflected light intensity at 1440 nm, $I_o$ is the initial light intensity at 1440 nm, L is the total light path length, $\mu_s^{1440}$ is the scattering coefficient of the tissue at 1440 nm, and $\mu_a^{1440}$ is the absorption coefficient of the tissue at 1440 nm. The OCT profile at 1440 nm, along with the estimated scattering coefficient $\mu_s^{1440}$, can allow one to determine $\mu_a^{1440}$.

As previously mentioned, the outlined technique can also be used to determine scattering coefficients when a scattering profile utilizes a wavelength in which an absorption coefficient dominates (e.g., an absorption coefficient is measured using a wavelength where absorption dominates attenuation, followed by estimating an absorption coefficient at a second wavelength and determining the scattering coefficient at the second wavelength). Those skilled in the art will appreciate that the technique can also be applied with respect to other analytes besides water (e.g., hemoglobin) when appropriate wavelengths of light are chosen.

As discussed in U.S. application Ser. No. 10/916,236, the use of multiple wavelengths can also provide an additional sensor calibration technique. Using water detection as an exemplification of calibrating analyte effects on OCT measurements, the scattering coefficient of a first wavelength OCT measurement can drift even though the glucose concentration remains static because of the change in the scattering coefficient due to hydration changes. Thus, by measuring the skin hydration using a second wavelength in which the wavelength is selected such that the resulting scattering profile tracks hydration changes (e.g., the absorption coefficient at the second wavelength is high for water, and much higher relative to the absorption coefficient at the first wavelength), this drift can be compensated for and the OCT sensor can maintain calibration. Clearly, other analytes that can effect scattering coefficient measurements can also be compensated for using this technique.

Figure 8:
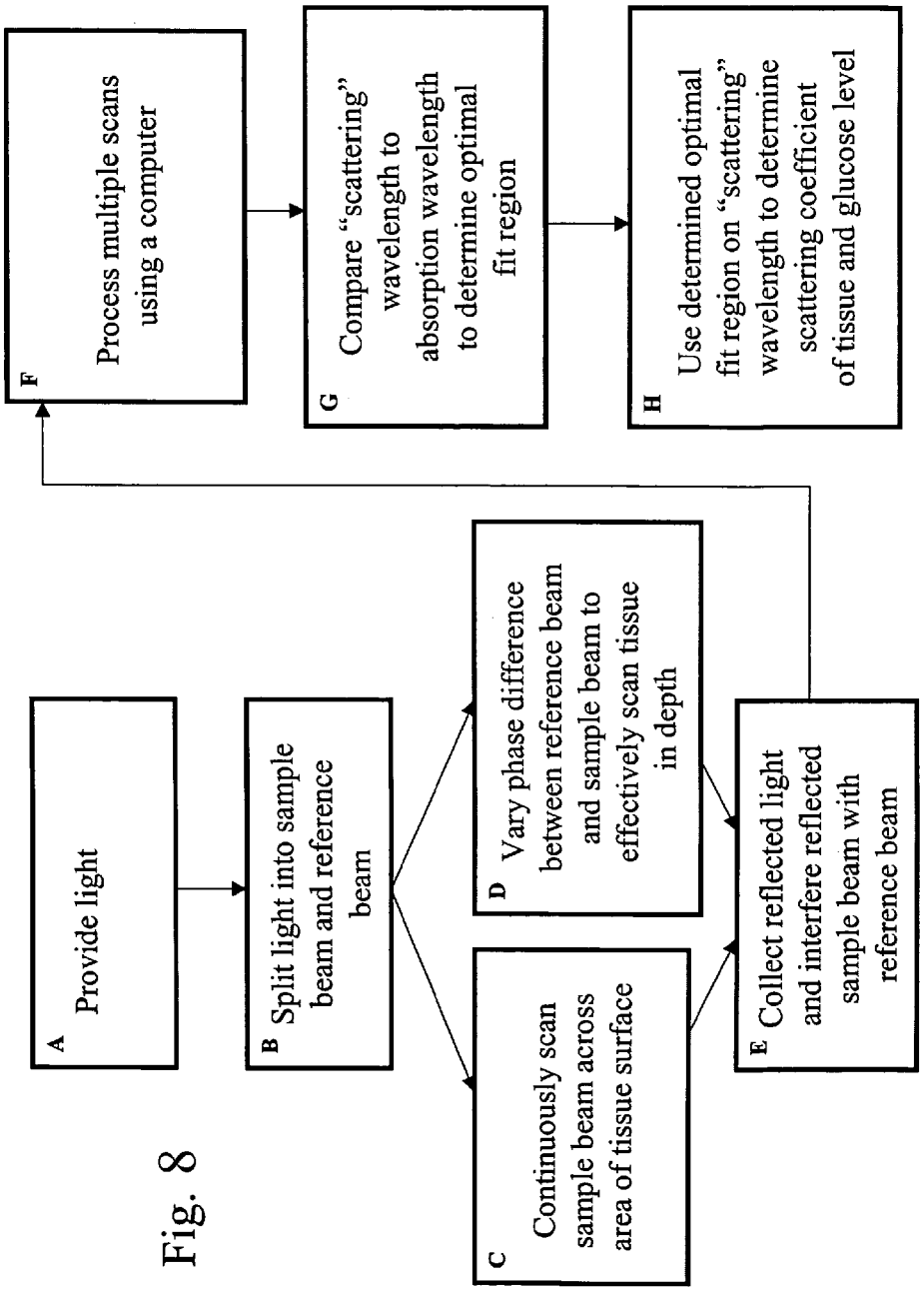
FIG. 8 is a schematic diagram illustrating a method of blood glucose monitoring in accordance with the disclosure.

FIG. 8 is a schematic block diagram of a method of measuring the blood glucose concentration on a human or animal subject. The first step, shown in Block A, is to provide light having scattering absorption or properties sensitive to glucose concentration within the tissue. Preferably the light provided comprises at least two different wavelengths. By different wavelengths is meant that the wavelengths should be sufficiently different that they have measurably different absorption and scatter properties for different levels of glucose and/or indicator components such as blood. Typically, the light is provided from multiple single wavelength sources, such as low coherence superluminescent diodes (SLEDs) at wavelengths in the red/near infrared range (RNIR). Alternatively, the light can be provided from a single broadband source appropriately notch filtered. Both wavelengths of light are advantageously directed in a single beam.

The next step, shown in Block B, is to split the single beam of light into a reference beam and a sample beam. The reference beam travels in an adjustable phase path denoted as the reference beam path (reference arm), and the sample beam travels in a sample beam path (sample arm) where it is directed onto the tissue to be monitored, e.g. the skin of a human diabetic. The light in the reference beam is directed over an adjustable phase path and will subsequently be interfered with sample light reflected from within the tissue.

In the third step, Block C, the sample beam is continuously or near continuously scanned over a two-dimensional area of the tissue while, at the same time, being interferometrically scanned in depth. Block D shows varying the phase (path length) of the reference beam so that light from the reference beam constructively interferes with reflected sample light from successively different depths of tissue. Block E shows the reflected light collected and interfered with the reference beam. As the interferometer sweeps in depth, the surface scan is also sweeping continuously. This "smears" out the scan and reduces the effect of speckle.

The next steps, Blocks F, G, and H are to process the resulting data to calculate glucose concentration. In essence, this is achieved by computing the scattering coefficient of glucose-containing tissue. Block F indicates the scanning data is input into a digital processor. Block G, which is optional, but advantageous, is to identify those scattering measurements that are from blood-perfused tissue (in or near blood vessels). Such identification can be accomplished, for example, by providing light of two different wavelengths, at least one of which scatters from blood-perfused tissues in a characteristic manner. Finally, in Block H, the scattering coefficient of the glucose containing tissue is calculated, and the correlated glucose level in blood is determined.

Figure 9:
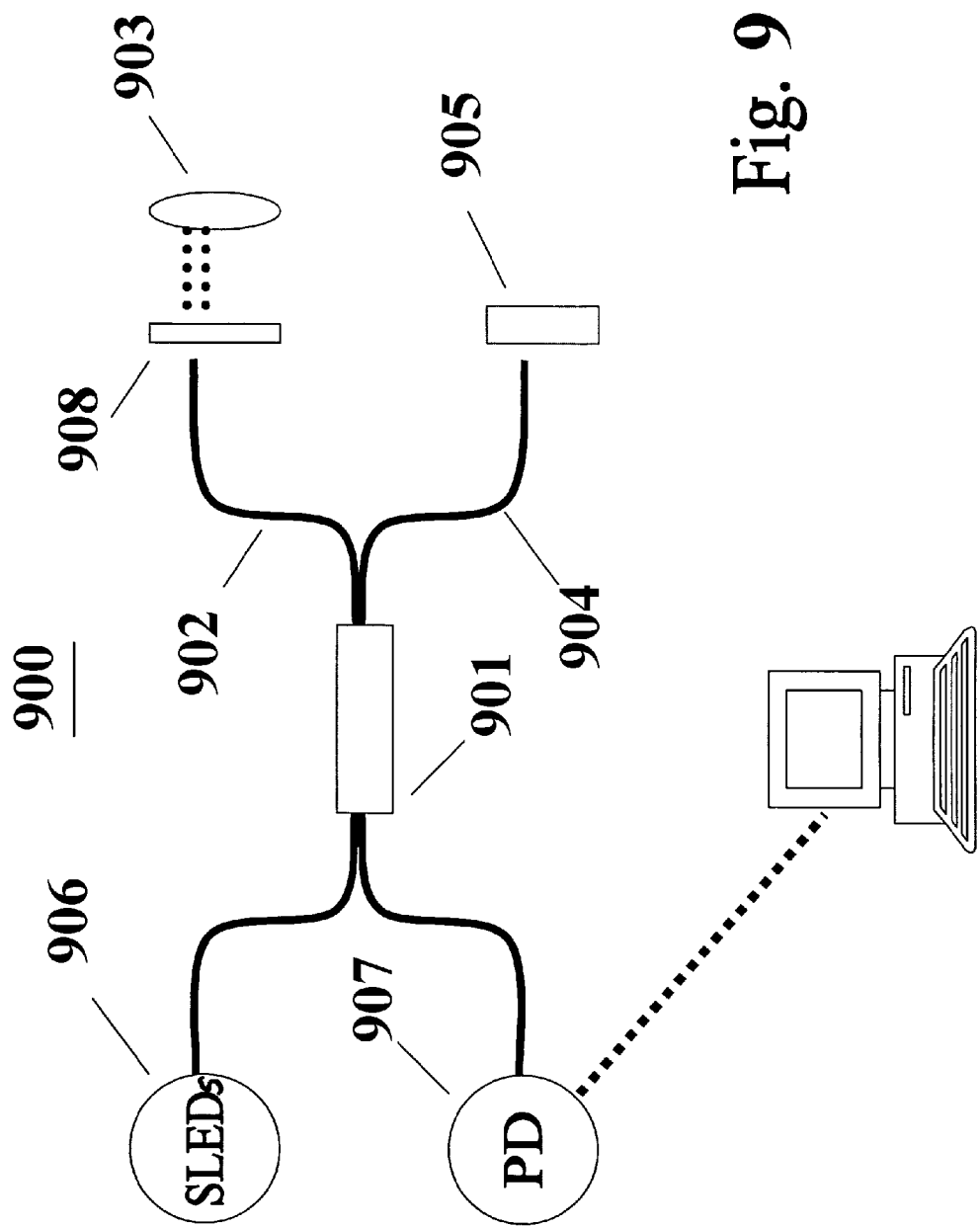
FIG. 9 schematically illustrates an apparatus useful for practicing the method of FIG. 8.

FIG. 9 schematically shows advantageous apparatus 900 for practicing the method of FIG. 8. The apparatus 900 comprises a fiber optics based low coherence interferometer (LCI). A 2×2 fiber optic splitter 901 forms the basic interferometer. An optical input from light sources 906 is split between a sample beam 902 and a reference beam 904. Sample light in beam 902 is continuously scanned across a sample surface by scanner 908. Preferably, the end of the sample beam 902 can contain imaging optics 903 to tailor the spot size according to the area tissue being measured. Reference beam 904 is varied or adjusted in phase as by a moveable minor 905 which can be vibrated or oscillated to scan depth. Reflected signals from beams 902 and 904 interfere and are presented to photodetector 907 for measurement. Advantageously, imaging optics 903 can provide high coupling efficiency between the optical system and the tissue.

The tissue volume with which the light interacts (referred to as the interaction volume) is determined by the spot size of the imaging optics (surface area) and the coherence length of the light (depth) The reference beam 904 has a scanning reflector 905 (such as a mirror). The reflector 905 of the interferometer determines the phase shift applied to the reference beam 904 and thus, which reflected light from the reference beam 904 will constructively interfere with the reflected sample beam 903. The differences in phase of the beams determines the depth from which scattered light will be measured. This can permit a fixed depth, adjustable depth, or a scan of multiple depths within the tissue. LCI is thus sensitive to the intensity of the reflected light localized in a small volume of tissue. Determination of the depth and interaction volume permits a more accurate selection of regions of blood-perfused tissue beneath the skin.

A photodetector 907 (such as a photodiode) can be used to measure the interference of the light from both the sample beam 902 and the reference beam 904. One or more photodetectors 907 may be used along with optical filters (not shown) designed for each of the different wavelength light sources 906 used in the measurement.

Preferably, the imaging optics 903 are beam focusing optics to reduce the beam cross section so as to minimize the region of optical interaction with the tissue. The use of these optics will enhance the selectivity of the signal while also reducing the effect of speckle.

Light passing through turbid biological tissue is subject to wavefront distortion that produces coherent noise or "speckle". The effect of speckle can be reduced by taking multiple scans from different locations on the tissue and then averaging these scans. This solution is impractical for the typical OCT imaging system, because the vast number of scans needed to reduce speckle would take too long and would produce a severe loss in the resolution of the image. However, for the present disclosure, the collection optics can be simpler. The present non-imaging system presents a practical solution to reducing coherent noise. Not only does the speckle effect significantly decrease, but the non-imaging system can continuously scan a two-dimensional area of tissue instead of being limited to a single scanning line. Area scans reduce speckle due to the diversity of tissue regions encompassed in the scan. They also maximize the coverage of blood-perfused tissue. Thus, coherent noise is also further reduced.

An alternative solution is to use parallel optical processing where multiple spots on the subject tissue are measured together to create "boiling" speckle. Boiling speckle occurs where the sub-spot speckle is changing so quickly that the observed speckle is averaged out by the human eye, or the integration time of the optical receiver. This inventive system may be modified to create boiling speckle by replacing the scanner 908 with either a lenslet array or a diffractive optical element (DOE). If the lenslet or DOE is rapidly translated or rotated about the optical axis at an very high speed, the observed speckle will be averaged out. Additionally, such a system reduces the number of scans required due to the greater variety of speckle detected.

Since glucose is delivered to the interstitial fluid (IF) in skin via blood, determining the scatter coefficient in the dermis layer of the tissue, where blood vessels are plentiful, provides the closest correlation to variations in glucose concentration. Again, an area scan increases the volume of blood-perfused tissue measured.

Area scanning could be achieved by a pair of rotating prisms that continuously move a sample beam spot over a circular area of the tissue surface. Advantageously, the spot would move a minimum of one spot diameter for each depth scan. Thus if the beam spot size is 12 microns and the depth scan is at a rate of 20 Hz, then the spot should advantageously be moved at a minimum rate of 240 microns per second and preferably much faster.

Spot diameters are typically in the range from about 10 microns to 100 microns and preferably 20 microns and higher.

The minimum area of the scan is defined by the number of spot diameters needed to move at the minimum depth scan rate. For the 12 micron spot and 20 Hz depth scan, the minimum area that would need scanning is about 2200 square microns, corresponding to a circular area of about 500 micron diameter. More preferably the system would be designed to cover an area corresponding to a diameter of 500 microns to 10,000 microns.

For speckle reduction using the boiling speckle method of noise reduction, the multiple spots would need to be moved quite rapidly. The spot should move at a minimum of one spot diameter in the integration time of the receiver. For individual spot sizes of about 10 microns and an integration time of about 4 microseconds, the spots would need to move at a minimum of $2.4 \times 10^5$ microns/sec.

The light sources 906 can be light emitting diodes (LED) or super luminescent diodes (SLEDs), both of which are semiconductor based light emitters whose wavelengths can be chosen to give the best contrast between absorption and scatter of blood and other biological constituents, such as water. Typically these wavelengths are in the red/near infrared (RNIR) region of the spectrum, however, longer and shorter wavelengths can be used for enhanced sensitivity. For the glucose measurements, two or more light sources are advantageous and can share the same optical paths through the interferometer.

One of the wavelengths can be chosen to have minimum absorption compared to the scattering coefficient for water and blood constituents. If the other wavelength is chosen to have peak absorption for certain biological constituents, then the difference in light attenuation between the two wavelengths can indicate the position in depth of a relevant structure, such as a blood vessel. Light from the two wavelengths is differently absorbed by the different constituents. This differential absorption differentially reduces the intensity of the scattered (reflected) light. Light reflected off the cellular membrane is partially absorbed by the respective constituent for that wavelength. Where the term "light is reflected from the blood" is used, it is understood to refer to light reflected from the cells in and around the blood vessels, and the constituent in the blood absorbs some of the light according to the specific wavelength and glucose level of the blood. These differences in the scattering and absorption properties provide for an optimal correlation between the scattered signal and blood glucose data.

One exemplary application is a first wavelength of about 1310 nm and a second wavelength of about 820-960 nm. A first wavelength of 1310 nm is chosen because the scattering properties of water and blood and blood constituents is at a maximum compared to the absorption properties of these fluids. The second wavelength, 820-960 nm, is chosen because the absorption of light is very high in the presence of hemoglobin, a blood constituent, (compared to the first wavelength). If the signal of the second wavelength were to experience a rapid decrease at a particular depth in the interaction volume, this rapid decrease would indicate the presence of hemoglobin, and hence, the location of blood-perfused tissue. It would thus indicate an optimal slope region for the scattering data of the first wavelength to be related to the glucose concentration.

A second example would be a first wavelength of about 1310 nm and a second wavelength of about 1450 nm. At this second wavelength, the scattering coefficients for blood and water are similar to those of the first wavelength. However, the absorption coefficient for water at this second wavelength is exponentially larger than that of the first wavelength. Thus, a differential measurement between these two wavelengths indicates changes in the hydration level of the tissue. Such changes can then be used to indicate an optimal slope region for measuring blood glucose. However, the use of these two specific wavelengths provides an additional benefit of sensor calibration. As the hydration level in the dermis layer varies, the scattering coefficient of the first wavelength may drift, even though the glucose concentration remains static. Thus, by measuring the skin hydration using the second wavelength, this drift can be compensated for and the OCT sensor can maintain calibration.

While the present invention has been described with respect to particular embodiments discussed herein, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A physiological monitoring system for determining a glucose level using an optical sensor, the system comprising:
   a non-invasive reflective optical sensor configured to provide light to biological tissue and receive reflected light from the biological tissue, wherein the light comprises two or more wavelengths selected to differentiate glucose from another biological constituent based on scattering properties of the light at the two or more wavelengths; and
   a physiological monitor comprising at least one processor, the physiological monitor configured to:
      determine first light scatter measurements based on reflected light at a first wavelength received by the non-invasive reflective optical sensor from the biological tissue using Optical Coherence Tomography, wherein the first light scatter measurements include measurements at a plurality of depths in the biological tissue;
      determine second light scatter measurements based on reflected light at a second wavelength received by the non-invasive reflective optical sensor from the biological tissue using Optical Coherence Tomography, wherein the second light scatter measurements include measurements at the plurality of depths in the biological tissue;
      subtract the first light scatter measurements from the second light scatter measurements to determine a differential data curve including differences between the first and second light scatter measurements at the plurality of depths;
      analyze the differential data curve to identify one or more peak data points;
      based on the one or more peak data points, identify an interval of the differential data curve indicative of glucose, wherein the interval of the differential data curve corresponds to an interval in the plurality of depths; and
      process a portion of the at least one of the first or second light scatter measurements that corresponds to the interval of the differential data curve to determine the glucose level of the biological tissue.

2. The system of claim 1, wherein the physiological monitor is further configured to process the portion of the at least one of the first or second light scatter measurements to determine the glucose level based at least partly on the scattering properties of the light.

3. The system of claim 1, wherein the non-invasive reflective optical sensor is configured to generate a reference beam that is adjusted to constructively interfere with the reflected light from the biological tissue.

4. The system of claim 1, wherein the reflected light includes light reflected from glucose in the biological tissue.

5. The system of claim 1, wherein the two or more wavelengths each have different scattering properties for glucose-containing tissues from the other.

6. The system of claim 5, wherein the two or more wavelengths comprise wavelengths at 1310 nm, and either 1450 nm or 820-960 nm.

7. The system of claim 5, wherein at least one of the two or more wavelengths of light is infrared or near infrared light.

8. The system of claim 5, wherein differences in the scattering properties of the light at the two or more wavelengths indicates the presence of glucose.

9. The system of claim 1, wherein the physiological monitor is further configured to:
   normalize the first and second light scatter measurements.

10. A method of measuring glucose concentration within biological tissue, the method comprising:
    generating a beam of light, the beam comprising two or more wavelengths selected to differentiate glucose from another biological constituent based on scattering properties of the beam; and
    illuminating biological tissue with the beam;
    determining first light scatter measurements based at least partly on light from the beam at a first wavelength reflected by the illuminated biological tissue using Optical Coherence Tomography, wherein the first light scatter measurements include measurements at a plurality of depths in the biological tissue;
    determining second light scatter measurements based at least partly on light from the beam at a second wavelength reflected by the illuminated biological tissue using Optical Coherence Tomography, wherein the second light scatter measurements include measurements at the plurality of depths in the biological tissue;
    subtracting the first light scatter measurements from the second light scatter measurements to determine a differential data curve including differences between the first and second light scatter measurements at the plurality of depths;
    analyzing the differential data curve to identify one or more peak data points;
    based on the one or more peak data points, identifying an interval of the differential data curve indicative of glucose, wherein the interval of the differential data curve corresponds to an interval in the plurality of depths; and
    processing a portion of the at least one of the first or second light scatter measurements that corresponds to the interval of the differential data curve to determine a glucose level of the biological tissue.

11. The method of claim 10 further comprising:
    generating a reference beam and interfering said reference beam with the light from the beam to determine the first and second light scatter measurements.

12. The method of claim 10, wherein the two or more wavelengths each have different scattering properties for glucose-containing tissues from the other.

13. The method of claim 12, wherein the two or more wavelengths comprise wavelengths at 1310 nm, and either 1450 nm or 820-960 nm.

14. The method of claim 12, wherein at least one of the two or more wavelengths of light is infrared or near infrared light.

15. The method of claim 12, wherein differences in the scattering properties of the beam at the two or more wavelengths indicates the presence of glucose.

16. The method of claim 12, wherein the at least two wavelengths are selected to accentuate contrast between glucose and one or more other biological constituents.

17. The method of claim 16, wherein the one or more other biological constituents are located around the glucose.

18. The method of claim 10, wherein the beam comprises at least three wavelengths, each having different scattering properties for glucose-containing tissues from the other.

19. The method of claim 10, wherein the glucose level is estimated based at least partly on identifying glucose using light scatter measurements corresponding to one or more blood vessels.

20. The method of claim 10, wherein the light from the beam reflected by the illuminated biological tissue includes light reflected from glucose in the illuminated biological tissue.

21. The method of claim 10 further comprising:
   normalizing the first and second light scatter measurements.

* * * * *